(12) United States Patent
Meyers et al.

(10) Patent No.: US 8,980,247 B2
(45) Date of Patent: Mar. 17, 2015

(54) PARVOVIRUS METHODS AND COMPOSITIONS FOR KILLING NEOPLASTIC CELLS

(75) Inventors: Craig M. Meyers, Hummelstown, PA (US); Samina Alam, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 73 days.

(21) Appl. No.: 13/324,484

(22) Filed: Dec. 13, 2011

(65) Prior Publication Data

US 2012/0213736 A1    Aug. 23, 2012

Related U.S. Application Data

(63) Continuation-in-part of application No. 11/577,782, filed as application No. PCT/US2005/037930 on Oct. 21, 2005, now Pat. No. 8,080,240.

(60) Provisional application No. 60/620,928, filed on Oct. 21, 2004.

(51) Int. Cl.
| | |
|---|---|
| *C12N 15/35* | (2006.01) |
| *C12N 7/00* | (2006.01) |
| *C07K 14/005* | (2006.01) |
| *C12N 15/864* | (2006.01) |
| *A61K 38/00* | (2006.01) |

(52) U.S. Cl.
CPC ............... *A61K 35/768* (2013.01); *C12N 7/00* (2013.01); *C12N 2750/14132* (2013.01); *C12N 2750/14133* (2013.01); *A61K 38/00* (2013.01); *C07K 14/005* (2013.01); *C12N 2750/14122* (2013.01)
USPC ....................................................... 424/93.3

(58) Field of Classification Search
CPC ........... C12N 2750/14145; C12N 2750/14162; C12N 2800/50; C12N 2830/85; C12N 2799/025; C12N 2750/14332; C12N 2750/1401; C12N 2750/14122; C12N 2750/14133; C12N 2750/14322; A61K 35/768; A61K 38/00; A61K 48/0058
See application file for complete search history.

(56) References Cited

U.S. PATENT DOCUMENTS 8,080,240 B2 *  12/2011  Meyers et al. ............... 424/93.1

OTHER PUBLICATIONS

Duverger et al. Cancer Diagnosis and Therapy 2001, vol. 97, Issue 5, pp. 706-712.*
Zhou et al. Biochimica et Biophysica Acta (BBA)—Gene Structure and Expression, 1999, vol. 1444, Issue 3, pp. 371-383.*
Berns K. Microbiological Reviews, 1990, pp. 316-329.
Coker, et al., "Experimental and Molecular Pathology", 2001, vol. 70, No. 2, pp. 83-89.
Eisold, et al., "Int. J. Cancer", 2002, vol. 100, pp. 606-614.
Fan, P-D., "Replication or rep-cap Gene is Essential for the High-Effeciency Production of Recombinant AAV.", Human Gene Therapy, 8:87-98 (1997).
Klein-Bauernschmitt, et al., "European Journal of Cancer", 1996, vol. 32A, No. 100, pp. 1774-1780.
Moehler, M., et al., "Effective infection, apoptotic cell killing and gene transfer of human hepatoma cells but not primary hepatocytes by arvovirus H1 and derived vectors", Cancer Gene Therapy, 8(3):158-167 (2001).
Olijslagers, A., et al., "Potentiation of a recombinant oncolytic parvovirus by expression of apoptin", Cancer Gene Therapy, 8(12):958-965 (2001).
Rohr, U-P., et al., "Non-small lung cancer cells are prime targets for p53 gene transfer medicated by a recombinant adeno-associated virus type-2 vector", Cancer Gene Therapy, 10:898-908 (2003).
Smith, E., et al., "Oncolytic viruses as novel anticancer agents: turning one scourge against another", Exp. Pin. Drugs, 9(2):311-327 (2000).
Wollmann, G. et al., "Targeting Human Glioblastoma Cells: Comparison of Nine Viruses with Oncolytic Potential", J. Virol. 79(10:6005-6022 (2005).

* cited by examiner

*Primary Examiner* — Bao Li
(74) *Attorney, Agent, or Firm* — McKee, Voorhees & Sease

(57) ABSTRACT

According to the invention, parvoviruses such as the adeno-associated virus Type 2 (AAV2) are found to be oncolytic, selectively mediating apoptosis in cancer cells and their precursors, while leaving healthy cells intact. The invention also includes a method of killing cancer and other neoplastic and preneoplastic cells by administrating to said cells the AAV2 proteins Rep78 or Rep 68, expression constucts encoding the same, or pharmaceutical compositions comprising the same.

8 Claims, 10 Drawing Sheets

PARVOVIRUS METHODS AND COMPOSITIONS FOR KILLING NEOPLASTIC CELLS

CROSS-REFERENCE TO RELATED APPLICATIONS

This application is a continuation-in-part of U.S. Ser. No. 11/577,782 filed on Apr. 23, 2007, which application is based on PCT/US05/37930 filed on Oct. 21, 2005, which is a conversion of and claims priority to U.S. Provisional Patent Application No. 60/620,928 filed Oct. 21, 2004, all of which are herein incorporated by reference in their entirety.

GRANT REFERENCE

This invention was made with government support under NIH Grant Number CA79006 awarded by United States Government National Institutes of Health. The government has certain rights in the invention.

BACKGROUND OF THE INVENTION

The limited ability of anti-neoplastic therapy to distinguish neoplastic from normal cells continues to be a primary hurdle in the treatment and irradiation of neoplastic, tumor or other cancerous cells. Distinguishing between the two on the basis of proliferative behavior has shown some success, but the search for biochemical characteristics of neoplastic cells that are tumor specific rather than proliferation specific remains the focus of further research. Unfortunately current molecular genetic studies have failed to support the expectation that such characteristics are a consistent feature of neoplastic cells. Rather these studies suggest that the neoplastic state can be explained without postulating tumor specific functions, but merely the operation of normal proliferation-specific functions at abnormal levels, as a result of changes (sometimes minimal) in the structure of growth-regulatory genes or changes in their number or chromosomal environment. This conclusion suggests that continued search for highly specific attributes of neoplastic cells cannot be relied upon for a general solution to the problems of cancer therapy.

As can be seen there is a continuing need in the art for cancer therapy that specifically and selectively targets and kills cancer cells and their precursors.

In general, gene therapy for cancers and many diseases offers novel treatment strategies and leads to the destruction of malignant and suboptimal cells. Ideally, the goal in all cases is to target deregulated cells while leaving the surrounding cells healthy and intact. Major cancer therapy approaches have included chemosensitization, cytokine gene transfer, inactivation of proto-oncogene expression, replacement of defective tumor suppressor genes, and transduction of oncolytic viruses. Included in this category are Adeno-associated virus-derived vectors which have been shown to be nonpathogenic vectors with potential for cancer gene therapy.

SUMMARY OF THE INVENTION

According to the invention, applicants have found that parvoviruses such as the adeno-associated virus Type 2 (AAV2) selectively mediate cell death including but not limited to apoptosis in cancer cells and their precursors, while leaving healthy cells intact. The invention thus comprises a method of killing cancer and other neoplastic and preneoplastic cells by administration of AAV2 virus, viral particles, products or replication incompetent vectors derived there from to said cells. AAV2 is a non-pathogenic tumor suppressive virus which has been shown to perturb cell cycle regulation of infected cells. Applicants have surprisingly found that administration of AAV2, its protein products or viral particles to cancer cells and/or their precursors results in cell death of cancer cells in approximately 6 days post infection while similar administration to noncancerous cells results in no such effects.

In a preferred embodiment the AAV2 viral particles are created in vivo with the presence of a helper virus including but not limited to HPV, adenovirus, herpesvirus, or vaccinia virus provides for enhancer/helper functions for replication of AAV and virus production in the cell. In a most preferred embodiment the method is used to kill cancer cells and their precursors which are known to be associated with the presence of one of the aforementioned helper viruses, such as cervical cancer cells which are associated with the presence of HPV virus.

Also included in the invention are pharmaceutical compositions for killing cancer cells which includes an AAV2 virus, an AAV2 virus particle or an AAV2 vector wherein the AAV2 virus itself is the therapeutic agent, further compositions include AAV2 gene products (rep proteins), genomic AAV2 sequences (such as ITR hair-pin ends), capsid proteins, or other treatment protocols which activate the same cell signaling pathways activated upon virus binding to cell surface receptors. While not wishing to be bound by any theory, it is postulated that the proteins produced by parvoviruses, (rep proteins), the nucleotide hairpin ends, or possibly the capsid proteins produced by the virus cause the desired effects. The invention also contemplates use of other elements which will activate the identical pathways as the parvovirus AAV2, according to the descriptions herein.

Applicants have further demonstrated that this cell death is apoptotic in nature and occurs during all stages of carcinogenic progression. Thus invention also includes prophylactic treatment for cancer prevention for treating all stages of cancer including the earliest stages that may be undetectable by clinical observations as normal, non-cancerous cells infected by AAV2 did not undergo apoptosis and displayed no cytopathic effects.

Applicants have also identified specific AAV proteins that are involved in inducing apoptosis in the cancer cells. According to the invention AAV2 Rep proteins, particularly Rep 78 and Rep 68 acting alone or in concert, trigger the increased S phase entry and the downstream cell death process in cancer cells.

Thus the invention includes methods of preventing or treating cancer in patients comprising introducing an AAV2 Rep proteins associated with cancer cell apoptosis to said patient. In a preferred embodiment the AAV2 Rep protein is Rep 68 and/or Rep 78. The invention also includes pharmaceutical compositions including an AAV2 Rep proteins such as Rep 68 and Rep 78 and a carrier. The invention also includes methods of treating of preventing cancer in a patient by introducing to said patient a polynucleotide sequence which includes an expression construct for a AAV2 Rep protein. Pharmaceutical compositions including such expression constructs are also within the scope of the invention.

DETAILED DESCRIPTION OF THE INVENTION

Figure 1:
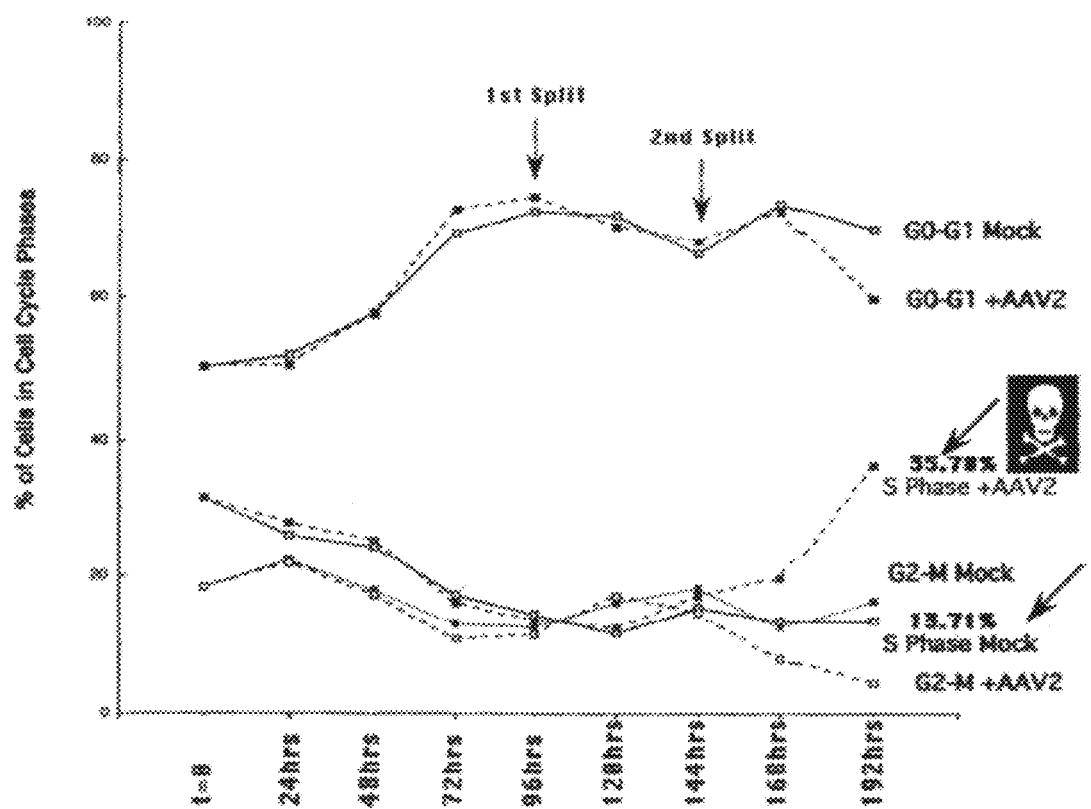
FIG. 1 is a graph showing the percentage of cells in cell cycle phase over time. FACS analysis of the mock and AAV2 infected cells suggested that massive cell death was accompanied by a more than 20% increase in the number of cells with S phase DNA content.

The present invention provides a method of treating a neoplasm in an animal by using an oncolytic virus, particularly a Parvovirus, such as AAV2. According to the invention Applicants have determined that the virus AAV2 and/or its viral proteins are oncolytic to a variety of cancer cells. The cell killing was demonstrated both with and without the presence of helper virus.

Because the AAV2 virus is nonpathogenic, the virus or its proteins may be used in a prophylactic protocol to protect a patient from cancer. According the this embodiment a patient at risk for neoplasia may be treated by administration of the AAV2 virus or proteins as described herein.

Prior to describing the invention in further detail, the terms used in this application are defined as follows unless otherwise indicated.

DEFINITIONS

A "neoplastic cell", "tumor cell", or "cell with a proliferative disorder" refers to a cell which proliferates at an abnormally high rate. A new growth comprising neoplastic cells is a "neoplasm", also known as a "tumor". A tumor is an abnormal tissue growth, generally forming a distinct mass that grows by cellular proliferation more rapidly than normal tissue growth. A tumor may show partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant tumors arising from epithelial structures are called carcinomas; malignant tumors that originate from connective tissues such as muscle, cartilage, fat, or bone are called sarcomas; and malignant tumors affecting hematopoietic structures (structures pertaining to the formation of blood cells) including components of the immune system, are called leukemias and lymphomas. Other tumors include, but are not limited to neurofibromatosis.

A "mutation" may be a deletion, insertion, or substitution of any nucleotide(s) or amino acid(s).

"Infection by parvovirus" refers to the entry and replication of Parvovirus in a cell. Similarly, "infection of a tumor by parvovirus" refers to the entry and replication of parvovirus in the cells of the tumor.

"AAV2" refers to any virus whether naturally occurring, modified or recombinant which retains the oncolytic properties of the AAV2 viruses described herein.

"Helper virus" refers to any virus or viral particle that helps the AAV2 to replicate. Helper viruses include but are not limited to adenovirus, herpesvirus, vaccinia virus, or human papillomaviruses or their helper proteins.

The AAV2 virus may be naturally occurring or modified. The virus is "naturally occurring" when it can be isolated from a source in nature and has not been intentionally modified by humans in the laboratory. For example, the adeno associated virus can be from a "field source", that is, from a human who has been infected with the virus.

The efficacy of the compositions of the invention in treating or preventing a particular disease, disorder, or condition can be evaluated both in vitro and in vivo. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to cancer, treatment may be measured quantitatively or qualitatively to determine the presence/absence of the disease, or its progression or regression using, for example, reduction in tumor size, a reduction in the rate of metastasis, and/or a slowing of tumor growth, and/or no worsening in disease over a specified period of time or other symptoms associated with the disease or clinical indications associated with the pathology of cancer development.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/ 6×SSC/0.1% SDS/100 µg/ml ssDNA, in which temperatures for hybridization are above 37 degrees C. and temperatures for washing in 0.1×SSC/0.1% SDS are above 55 C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

AAV2 Polynucleotides (Encoding Rep 68 and Reo 78)

One aspect of the invention provides polynucleotides corresponding or complementary to all or part of an AAV2 Rep protein, preferably Rep 68 and/or Rep 78 gene, mRNA, and/or coding sequence, preferably in isolated form, including polynucleotides encoding a AAV2 Rep protein and fragments thereof, DNA, RNA, DNA/RNA hybrid, and related molecules, polynucleotides or oligonucleotides complementary to a AAV2 Rep protein gene or mRNA sequence or a part thereof, and polynucleotides or oligonucleotides which hybridize to a AAV2 Rep gene, mRNA, or to an AAV2 Rep-encoding polynucleotide (collectively, "AAV2 Rep polynucleotides"). As used herein, the AAV2 Rep 78 or Rep 68 gene and protein is meant to include the Rep 68 or Rep 78 gene and protein specifically described herein and the genes and proteins corresponding to other Rep 68 or Rep 78 proteins and structurally similar variants of the foregoing. Such other Rep 68 or Rep 78 proteins and variants will generally have coding sequences which are highly homologous to the Rep 68 or Rep 78 and/or Rep 68 or Rep 78 coding sequences, and preferably will share at least about 50% amino acid identity and at least about 60% amino acid homology (using BLAST criteria), more preferably sharing 70% or greater homology (using BLAST criteria).

A Rep 78 or Rep 68 polynucleotide may comprise a polynucleotide having the nucleotide sequence of human Rep 78 or Rep 68 as shown in SEQ ID NO:1 or 3, a sequence complementary to the foregoing, or a polynucleotide fragment of any of the foregoing. Another embodiment comprises a polynucleotide which is capable of hybridizing under stringent hybridization conditions to the Rep 78 or Rep 68 cDNA shown in SEQ ID NO:1 or 3 or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules, such as phosphorothioate derivatives, that specifically bind DNA or RNA in a base pair-dependent manner. A skilled artisan can readily obtain these classes of nucleic acid molecules using the Rep 78 or Rep 68 polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a Rep 78 or Rep 68 polynucleotide in a sample and as a means for detecting a cell expressing a Rep 78 or Rep 68 protein. Examples of such probes include polypeptides comprising all or part of the human Rep 78 or Rep 68 cDNA sequence shown in FIG. 1. Examples of primer pairs capable of specifically amplifying Rep 78 or Rep 68 mRNAs are also described in the Examples which follow. As will be understood by the skilled artisan, a great many different primers and probes may be prepared based on the sequences provided in herein and used effectively to amplify and/or detect a Rep 78 or Rep 68 mRNA.

As used herein, a polynucleotide is said to be "isolated" when it is substantially separated from contaminant polynucleotides which correspond or are complementary to genes other than the Rep 78 or Rep 68 gene or which encode polypeptides other than Rep 78 or Rep 68 gene product or fragments thereof. A skilled artisan can readily employ nucleic acid isolation procedures to obtain an isolated Rep 78 or Rep 68 polynucleotide.

Methods for Isolating Rep 78 or Rep 68-Encoding Nucleic Acid Molecules

The Rep 78 or Rep 68 cDNA sequences described herein enable the isolation of other polynucleotides encoding Rep 78 or Rep 68 gene product(s), as well as the isolation of polynucleotides encoding Rep 78 or Rep 68 gene product homologues, alternatively spliced isoforms, allelic variants, and mutant forms of the Rep 78 or Rep 68 gene product. Various molecular cloning methods that can be employed to isolate full length cDNAs encoding a Rep 68 or Rep 78 gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., eds., Wiley and Sons, 1995). For example, lambda phage cloning methodologies may be conveniently employed, using commercially available cloning systems (e.g., Lambda ZAP Express, Stratagene). Phage clones containing Rep 68 or Rep 78 gene cDNAs may be identified by probing with a labeled Rep 78 or Rep 68 cDNA or a fragment thereof. For example, in one embodiment, the Rep 68 or Rep 78 nucleic acid sequence (SEQ 1N NO: 1 and 3) DNA or a portion thereof can be synthesized and used as a probe to retrieve overlapping and full length cDNAs corresponding to a Rep 68 or Rep 78 gene. The Rep 68 or Rep 78 gene itself may be isolated by screening genomic DNA libraries, bacterial artificial chromosome libraries (BACs), yeast artificial chromosome libraries (YACs), and the like, with Rep 68 or Rep 78 DNA probes or primers.

Recombinant DNA Molecules and Host-Vector Systems

The invention also provides recombinant DNA or RNA molecules containing a Rep 68 or Rep 78 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al., 1989, supra).

The Invention further provides a host-vector system comprising a recombinant DNA molecule containing a Rep 78 or Rep 68 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HghFive cell). Examples of suitable mammalian cells include various prostate cancer cell lines such LnCaP, PC-3, DU145, LAPC-4, TsuPrl, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a Rep 78 or Rep 68 may be used to generate Rep 78 or Rep 68 proteins or fragments thereof using any number of host-vector systems routinely used and widely known in the art.

A wide range of host-vector systems suitable for the expression of Rep 78 or Rep 68 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, Rep 78 or Rep 68 may be preferably expressed in several prostate cancer and non-prostate cell lines, including for example 293, 293T, rat-1, 3T3, PC-3, LNCaP and TsuPrl. The host-vector systems of the invention are useful for the production of a Rep 78 or Rep 68 protein or fragment thereof. Such host-vector systems may be employed to study the functional properties of Rep 78 or Rep 68 and Rep 78 or Rep 68 mutations.

Recombinant human 161P2F10B protein or an analog or homolog or fragment thereof can be produced by mammalian cells transfected with a construct encoding a 161P2F10B-related nucleotide. For example, 293T cells can be transfected with an expression plasmid encoding 161P2F10B or fragment, analog or homolog thereof, a 161P2F10B-related protein is expressed in the 293T cells, and the recombinant 161P2F10B protein is isolated using standard purification methods (e.g., affinity purification using anti-161P2F10B antibodies). In another embodiment, a 161P2F10B coding sequence is subcloned into the retroviral vector pSRαMSVt-kneo and used to infect various mammalian cell lines, such as NIH 3T3, TsuPrl, 293 and rat-1 in order to establish 161P2F10B expressing cell lines. Various other expression systems well known in the art can also be employed. Expression constructs encoding a leader peptide joined in frame to a 161P2F10B coding sequence can be used for the generation of a secreted form of recombinant 161P2F10B protein.

As discussed herein, redundancy in the genetic code permits variation in Rep 68 or Rep 78 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, Mol. Cell. Biol., 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)). Mature recombinant human Rep 78 or Rep 68 protein may be produced and secreted by mammalian cells transfected with a construct encoding precursor Rep 78 or Rep 68. In a particular embodiment described in the Examples, 293T cells are transfected with an expression plasmid encoding the precursor form of Rep 78 or Rep 68 (i.e., including the signal sequence) and mature Rep 78 or Rep 68 protein is secreted into the cell culture medium where it may be conveniently isolated using standard purification methods. Mature recombinant human Rep 78 or Rep 68 may also be produced by cells which process but do not secrete the mature protein. One example of such a system is a Rep 78 or Rep 68 encoding baculovirus-infected cell. As described in the examples, such cells express and process high levels of Rep 78 or Rep 68 intracellularly. The mature Rep 78 or Rep 68 protein may be recovered, in such cases, from cell lysates using standard procedures. Whether the mature Rep 78 or Rep 68 is secreted or is retained intracellularly by the host cell, Rep 78 or Rep 68 may be affinity purified from media or cell lysates using Rep 78 or Rep 68 antibodies.

Proteins encoded by the Rep 78 or Rep 68 genes, or by fragments thereof, will have a variety of uses, including but not limited therapeutic methods in the management of human cancers.

Rep 78 or Rep 68 Proteins

Another aspect of the present invention provides Rep 78 or Rep 68 proteins and polypeptide fragments thereof. The Rep 78 or Rep 68 proteins of the invention include those specifically identified herein, as well as allelic variants, conservative substitution variants and homologs that can be isolated/generated and characterized without undue experimentation following the methods outlined below. Fusion proteins which combine parts of different Rep 78 or Rep 68 proteins or fragments thereof, as well as fusion proteins of a Rep 78 or Rep 68 protein and a heterologous polypeptide are also included. Such Rep 78 or Rep 68 proteins will be collectively referred to as the Rep 78 or Rep 68 proteins, the proteins of the invention, or Rep 78 or Rep 68. As used herein, the term "Rep 78 or Rep 68 polypeptide" refers to a polypeptide fragment or a Rep 78 or Rep 68 protein of at least 10 amino acids, preferably at least 15 amino acids that are able to retain biological activity of the Rep protein.

A specific embodiment of a Rep 78 or Rep 68 protein comprises a polypeptide having the amino acid sequence of human Rep 78 or Rep 68 as shown in SEQ ID NO:2 or 4. In general, naturally occurring allelic variants of human Rep 78 or Rep 68 will share a high degree of structural identity and homology (e.g., 90% or more identity). Typically, allelic variants of the Rep 78 or Rep 68 proteins will contain conservative amino acid substitutions within the Rep 78 or Rep 68 sequences described herein or will contain a substitution of an amino acid from a corresponding position in a Rep 78 or Rep 68 homologue. One class of Rep 78 or Rep 68 allelic variants will be proteins that share a high degree of homology with at least a small region of a particular Rep 78 or Rep 68 amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Rep 78 or Rep 68 proteins may be embodied in many forms, preferably in isolated form. As used herein, a protein is said to be "isolated" when physical, mechanical or chemical methods are employed to remove the Rep 78 or Rep 68 protein from cellular constituents that are normally associated with the protein. A skilled artisan can readily employ standard purification methods to obtain an isolated Rep 78 or Rep 68 protein. A purified Rep 78 or Rep 68 protein molecule will be substantially free of other proteins or molecules which impair the binding of Rep 78 or Rep 68 to antibody or other ligand. The nature and degree of isolation and purification will depend on the intended use. Embodiments of a Rep 78 or Rep 68 protein include a purified Rep 78 or Rep 68 protein and a functional, soluble Rep 78 or Rep 68 protein. In one form, such functional, soluble Rep 78 or Rep 68 proteins or fragments thereof retain the ability to bind antibody or other ligand.

The invention also provides Rep 78 or Rep 68 polypeptides comprising biologically active fragments of the Rep 78 or Rep 68 amino acid sequence, such as a polypeptide corresponding to part of the amino acid sequences for Rep 78 or Rep 68 as shown in SEQ 1N NO:2 or 4. Such polypeptides of the invention exhibit properties of the Rep 78 or Rep 68 protein, such as the ability to induce apoptosis in cancer cells.

Rep 78 or Rep 68 polypeptides can be generated using standard peptide synthesis technology or using chemical cleavage methods well known in the art based on the amino acid sequences of the human Rep 78 or Rep 68 proteins disclosed herein. Alternatively, recombinant methods can be used to generate nucleic acid molecules that encode a polypeptide fragment of a Rep 78 or Rep 68 protein. In this regard, the Rep 78 or Rep 68-encoding nucleic acid molecules described herein provide means for generating defined fragments of Rep 78 or Rep 68 proteins. Rep 78 or Rep 68 polypeptides are particularly useful in generating and characterizing domain specific antibodies (e.g., antibodies recognizing an extracellular or intracellular epitope of a Rep 78 or Rep 68 protein), in identifying agents or cellular factors that bind to Rep 78 or Rep 68 or a particular structural domain thereof, and in various therapeutic contexts, including but not limited to cancer vaccines. Rep 78 or Rep 68 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-Rep 78 or Rep 68 antibodies or in identifying cellular factors that bind to Rep 78 or Rep 68.

Therapeutic Methods and Compositions

Methods of treating cancer in mammals employ the sequences of the invention. This can include administration of the polynucleotide expression construct with a Rep 78 or Rep 68 sequence operable linked to a promoter for expression of the same in the host patient, or direct administration of the proteins sequences themselves. Either way, theses sequences form part of a pharmaceutical that may be administered any of a number of ways according to the invention. The AAV2 virus may be modified but still capable of lytically infecting a mammalian cell. The virus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The virus may be coated in a liposome or micelle. For example, the virion may be treated with chymotrypsin in the presence of micelle forming concentrations of alkyl sulfate detergents to generate a new infectious subvirion particle.

In certain embodiments, the entire AAV2 virus may be administered. The AAV2 virus may be a recombinant (i.e., reasserted) virus resulting from the recombination/reassortment of genomic segments from two or more genetically distinct adeno associated viruses. Recombination/reassortment of virus genomic segments may occur in nature following infection of a host organism with at least two genetically distinct viruses. Recombinant virions can also be generated in cell culture, for example, by co-infection of permissive host cells with genetically distinct viruses.

Accordingly, the invention contemplates the use of a recombinant AAV2 virus resulting from reassortment of genome segments from two or more genetically distinct AAV2 viruses. The invention further contemplates the use of recombinant viruses resulting from reassortment of genome. segments from two or more genetically distinct viruses wherein at least one parental virus is genetically engineered, comprises one or more chemically synthesized genomic segment, has been treated with chemical or physical mutagens, or is itself the result of a recombination event. The invention further contemplates the use of the recombinant AAV 2 virus that has undergone recombination in the presence of chemical mutagens, including but not limited to dimethyl sulfate and ethidium bromide, or physical mutagens, including but not limited to ultraviolet light and other forms of radiation.

The invention further contemplates the use of recombinant AAV2 viruses that comprise deletions or duplications in one or more genome segments, that comprise additional genetic information as a result of recombination with a host cell genome, or that comprise synthetic genes.

The AAV2 virus may be modified by incorporation of mutated coat proteins, such as for example, into the virion outer capsid. The proteins may be mutated by replacement, insertion, or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in AAV2 virus infected mammalian cells in vitro such as COS 1 cells will result in the incorporation of the mutated protein into the AAV2 virus virion particle (Turner and Duncan, 1992; Duncan et al., 1991; Mah et al., 1990).

While little or no host reaction was observed, the AAV2 virus may also be modified to even further reduce or eliminate an immune reaction to the virus. Such a modified virus is termed "immunoprotected AAV2 virus". Such modifications could include packaging of the virus in a liposome, a micelle, or other vehicle to mask the virus from the immune system. Alternatively, the outer capsid of the virus virion particle may be removed since the proteins present in the outer capsid are the major determinant of the host humoral and cellular responses.

An "immunoprotected virus" is a virus modified to reduce or eliminate an immune reaction to the virus. The modifications could include packaging of the virus in a liposome, a micelle, or other vehicle to mask the virus from the host immune system. Alternatively, the outer capsid of the virus virion particle may be removed since the proteins present in the outer capsid are the major determinant of the host humoral and cellular responses. In addition to reducing or eliminating immune responses, the modifications may also reduce non-specific uptake of the virus in normal tissues.

An "oncolytic virus" is a virus that preferentially replicates in, and kills, neoplastic cells. An oncolytic virus may be a naturally occurring virus or an engineered virus. Oncolytic viruses also encompass immunoprotected and reassortant viruses as described in detail for virus.

"Administration" of a virus to a subject refers to the act of administering the virus to a subject in a manner so that it contacts the target neoplastic and pre-neoplastic cells. The route by which the virus is administered, as well as the formulation, carrier or vehicle, will depend on the location as well as the type of the target cells.

The term "substantial lysis" means at least about 10% of the cells of a neoplasm are lysed. More preferably, at least about 20%, 30%, 40%, 50%, 60%, 70%, 80% or 90% of the cells are lysed. Most preferably, at least about 95% of the cells are lysed. The percentage of lysis can be determined, for example, by measuring the reduction in the size of the tumor or reduction of symptoms of the tumor.

A "mammal suspected of having a neoplasm" is a mammal that has a genetic disposition for a tumor, or a mammal in which the tumor or substantially all of the tumor has been surgically removed but is suspected of harboring residual tumor cells.

"Treating or alleviating a tumor" means alleviating or eliminating the symptoms of a tumor, or slowing down the progress of the tumor. The alleviation is preferably at least about 10%, more preferably at least about 20%, 30%, 40%, 50%, 60%, 70%, 80%, 90% or 95%.

A "metastatic tumor" is a tumor that has metastasized from a tumor located at another place in the same animal.

An "effective amount" is an amount of an agent that is sufficient to result in the intended effect. For an oncolytic virus used to treat or ameliorate a tumor, an effective amount is an amount of the virus sufficient to alleviate or eliminate the symptoms of the tumor or to slow down the progress of the tumor.

The terms "immunosuppressant" or "immune suppressive agent" include conventional immunosuppressants, immuno inhibitors, antibodies, and conditions such as radiation therapy or 11V infection which result in compromise of the immune system.

In addition to AAV2, other oncolytic viruses can be used in combination with AAV2 to practice the present invention in the same manner as AAV2. These viruses may be naturally existing, or they may be modified or mutated.

A few such oncolytic viruses are discussed below, and a person of ordinary skill in the art can practice the present invention using additional oncolytic viruses as well according to the disclosure herein and knowledge available in the art. The oncolytic virus may be a member in the family of myoviridae, siphoviridae, podoviridae, teciviridae, corticoviridae, plasmaviridae, lipothrixviridae, fuselloviridae, poxyiridac, iridoviridae, phycodnaviridae, baculoviridae, herpesviridae, adenoviridae, Papillomaviridae, polyomaviridae, polydnaviridae, inoviridae, microviridae, geminiviridac, circoviridae, hepadnaviridae, retroviridae, cyctoviridae, reoviridae, bimaviridae, paramyxoviridae, rhabdoviridae, filoviridae, orthomyxoviridae, bunyaviridae, arenaviridac, leviviridae, picornaviridae, sequiviridae, comoviridae, potyviridae, caliciviridae, astroviridae, nodaviridae, tetraviridae, tombusviridae, coronaviridae, glaviviridae, togaviridae, or barnaviridae. As with AAV2, immunoprotected or reassortant viruses of other oncolytic viruses are also encompassed in the present invention. Furthermore, a combination of at least two oncolytic viruses, including AAV2, can also be employed to practice the present invention.

The route by which the virus, Rep 68 or Rep78 protein, or nucleotide sequence encoding the same is administered, as well as the formulation, carrier or vehicle, will depend on the location as well as the type of the neoplasm. A wide variety of administration routes can be employed. For example, for a solid neoplasm that is accessible, the virus can be administered by injection directly to the neoplasm. For a hematopoietic neoplasm, for example, the virus can be administered intravenously or intravascularly. For neoplasms that are not easily accessible within the body, such as metastases or brain tumors, the virus is administered in a manner such that it can be transported systemically through the body of the mammal and thereby reach the neoplasm (e.g., intrathecally, intravenously, or intramuscularly). Alternatively, the virus can be administered directly to a single solid neoplasm, where it then is carried systemically through the body to metastases. The virus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation (e.g., for lung neoplasm).

The virus, protein, or DNA sequence can be administered systemically to mammals which are immune compromised or which have not developed immunity to the virus. In such cases, viruses that are administered systemically, i.e., by intravenous injection, will spread to the locations of the neoplastic cells, resulting in lysis of the cells.

This invention also includes pharmaceutical compositions which contain, as the active ingredient, one or more of the AAV2 viruses, expression constructs, AAV2 active proteins (Rep 68 or 78), hairpins, capsid proteins or any component which retains the oncolytic properties of the AAV2 virus as described herein, associated with pharmaceutically acceptable carriers or excipients. The invention further includes pharmaceutical compositions which contain, as the active ingredient, one or more of the viruses, DNA constructs, or Rep proteins along with an appropriate immunosuppressant, associated with pharmaceutically acceptable carriers or excipients. In making the compositions of this invention, the active ingredient/virus is usually mixed with an excipient, diluted by an excipient, or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propyl hydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/virus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device, or the nebulizing device may be attached to a face mask tent or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the virus of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on-demand delivery of pharmaceutical agents.

Other suitable formulations for use in the present invention can be found in Remington's Pharmaceutical Sciences.

The AAV2 virus DNA construct or Rep proteins and/or the pharmaceutical composition comprising the same may be packaged into convenient kits providing the necessary materials packaged into suitable containers. It is contemplated that the kits may also include chemotherapeutic agents and/or anti-antivirus antibody.

The AAV2, its Rep proteins, or DNA constucts are administered in an amount that is sufficient to treat the neoplasm (e.g., an "effective amount"). A neoplasm is "treated" when administration of virus to the proliferating cells effects lysis of the proliferating cells. This may result in a reduction in size of the neoplasm or a complete elimination of the neoplasm.

The reduction in size of the neoplasm, or elimination of the neoplasm, is generally caused by lysis of neoplastic cells ("oncolysis") by the virus. Preferably the effective amount is that amount able to inhibit tumor cell growth. Preferably the effective amount is from about 1.0 pfu/kg body weight to about $10^{15}$ pfu/kg body weight, and more preferably from about 102 pfu/kg body weight to about $10^{13}$ pfu/kg body weight. For example, for treatment of a human, approximately $10^2$ to $10^{17}$ pfU of equivalent number of infectious particles or equivalent MOI of virus can be used, depending on the type, size, and number of tumors present. The effective amount will be determined on an individual basis and may be based, at least in part, on consideration of the type of virus; the chosen route of administration; the individual's size, age, gender; the severity of the patient's symptoms; the size and other characteristics of the neoplasm; and the like. The course of therapy may last from several days to several months or until diminution of the disease is achieved.

The virus, Rep proteins, or DNA constructs can be administered in a single dose, or multiple doses (i.e., more than one dose). The multiple doses can be administered concurrently, or consecutively (e.g., over a period of days or weeks). The virus can also be administered to more than one neoplasm in the same individual.

The compositions are preferably formulated in a unit dosage form, each dosage containing from about $10^2$ pfus to about $10^{13}$ pfu of the virus. The term "unit dosage forms" refers to physically discrete units suitable as unitary dosages for human subjects and other mammals, each unit containing a predetermined quantity of virus calculated to produce the desired therapeutic effect, in association with a suitable pharmaceutical excipient.

It has been found that the virus, DNA construct or Rep proteins are effective for the treatment of solid neoplasms in immunocompetent mammals. Administration of unmodified virus directly to the neoplasm results in oncolysis of the neoplastic cells and reduction in the size of the tumor.

It is contemplated that the virus, DNA construct or Rep proteins may be administered in conjunction with surgery or removal of the neoplasm. Therefore, provided herewith are methods for the treatment of a solid neoplasm comprising surgical removal of the neoplasm and administration of a virus at or near to the site of the neoplasm.

It is contemplated that the virus may be administered in conjunction with or in addition to radiation therapy.

It is further contemplated that the virus, DNA construct or Rep proteins of the present invention may be administered in conjunction with or in addition to one or more known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracycline (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

The virus, DNA construct or Rep proteins of the present invention have been found to reduce the growth of tumors that are metastatic. In an embodiment of the invention, a method is provided for reducing the growth of metastatic tumors in a mammal comprising administering an effective amount of a virus to the mammal.

Applicants' studies have strongly correlated the ability of AAV2 infection to induce 100% cell death of multiple cancer cells. In all studies, cells were infected with an MOI of 0.02. Further, induction of cell death was correlated with AAV2 Rep protein expression, specifically Rep78, Rep68, Rep52 and Rep40. Expression of Rep proteins also coincided with increased entry of the AAV2 infected cells into the S phase of the cell cycle compared with uninfected controls. Since both Rep protein expression and increased entry into S phase coincided with death induction, it was hypothesized that expression of individual Rep proteins alone would induce the death process. In order to test whether the individual Rep proteins had the capability of inducing cell death, we transfected the Rep78 and Rep68 expression vectors into the MCF-7 breast cancer cell line. Using the calcium phosphate method of transfection, we routinely detect a transfection efficiency of about 25%-30%. Using this method we have also reported that transfection of the wild-type AAV2 genome alone into the MCF-7 breast cancer cells resulted in the appearance of damaged cell membranes which is also indicative of cell death. We observed that the Rep78 and Rep68 alone transfected cells did not show any evidence of cell death but that there was a 50% increase in the number of cells which entered S phase during late times in the experiment.

The outcomes of AAV2 infection regulated Rep protein expression versus transfection mediated expression of Rep78 and Rep68 are significantly different in that isolated expression of Rep78 and Rep68 alone caused a delayed entry of cells into S phase without inducing cell death. This suggests that to induce S phase entry coupled with cell death may require coordinated expression and functions of potentially all four Rep proteins. Also, our experiments potentially isolate the ability of at least the Rep78 and Rep68 proteins to induce S phase entry and related functions. Therefore, virus infection regulated Rep protein expression and downstream consequences are significantly different than expression of individual Rep proteins alone.

Since the whole AAV2 genome was needed to induce cell death in transfected MCF-7 cells, suggests that the AAV2 genomic single-stranded hair-pin ends may act in tandem with the Rep proteins to induce cell death. The single-stranded DNA may function to either induce of amplify the activity of cellular DNA damage response pathways. In this regard the Rep78 and Rep68 proteins can nick cellular DNA and also activate the DNA damage response pathways.

AAV2 binding, entry and infection of cells could activate multiple signaling pathways which affect transcription and translation of the Rep proteins from the early promoters of AAV2. Additionally, there is an additional possibility of post-translational modifications of the Rep proteins by these signaling pathways, which could affect their activity in terms of functions which regulate increased S phase entry and activation of death induction.

In order to further illustrate the present invention and advantages thereof, the following specific examples are given but are not meant to limit the scope of the claims in any way.

EXAMPLES

Example 1

Oncosuppressive Property of AAV2 is Mediated by Targeting Viral DNA Replication

AAV2 is ubiquitous, non-pathogenic, anogenital virus with tumor suppressive properties. Seroepidemiological data have clearly shown a negative association between AAV2 infection and the incidence of cervical cancer. In this respect, it is of interest to note that majority of the general population is seropositive for AAV2, whereas only a small fraction of patients with genital cancer were found to be seropositive for AAV2. Thus AAV2 exerts a protective effect against the development of cervical cancer. AAV2 is a helper-dependent, human Parvovirus, in that it requires the presence of helperviruses for its own replication. In turn, AAV inhibits the replication, transcription and virion morphogenesis of its helper virus. The mechanism of AAV2 mediated interference with its helper-virus life-cycle is related to its interference with helper-virus replication, promoter activates as well as oncogene expression. Thus far, the helper functions have been found to be provided by adenovirus, herpesvirus, or vaccinia virus. In addition, our laboratory has recently demonstrated that the human papillomaviruses are also capable of providing such helper functions.

A well characterized cell line in use in our laboratory is the CIN-612 9E cell line which maintains episomal copies of the Human Papillomavirus Type 3 1b (HPV3 1b). This cell line is a biopsy derived cell line from a patient with a low grade cervical lesion. Utilizing a HPV3 1b positive differentiation dependent organotypic raft culture system we have recently reported that HPV3 1b provides complete "enhancer/helper" functions for AAV2 replication and infectious virion morphogenesis. In turn, AAV2 inhibits the replication of HPV3 1b, thus decreasing the viral load and carcinogenic potential of the tissue.

AAV2 Can Also Mediate its Oncosuppressive Properties Via Modulation of the Cell Cycle In addition to interfering with helper virus DNA replication and promoter activity, AAV2 also mediates its oncosuppressive properties via perturbing cell cycle regulation. AAV2 infection has been shown to upregulate the expression of differentiation markers and markers of cellular senescence. AAV2 has the unique ability to mediate oncosuppressive effects via cell cycle modulation in naturally occurring tumor derived cell lines as well as cell lines which have been initiated with carcinogens. The ability of AAV2 to affect cell cycle regulation has been clearly demonstrated in a comprehensive study utilizing primary human fibroblasts derived from a tonsillectomy. In this study by Hermanns et. al, a thorough evaluation of the effect of AAV2 on cell cycle regulation in primary fibroblasts was presented. Infection was accompanied by Rb hypophosphorylation, suggesting a block in the G1 phase of the cell cycle. In addition, the expression of the universal CDK inhibitor p21/WAF1 was upregulated compared to mock samples. p21 is a unique CDK inhibitor in that it inhibits the activity of all cyclin-CDK complexes as well as being a potent tumor suppressor and regulator of cellular senescence. Although the results in the study by Hermanns et. al. clearly show cell cycle targeted effects of AAV2 in primary cells, one may argue that fibroblasts are not the normal host for AAV2. Rather, the anogenital localization of AAV2 places this virus in close proximity with the same tissue which could be infected by HPV suggesting that AAV2 also has tropism for keratinocytes.

We have previously demonstrated the negative effect of AAV2 on HPV replication in the differentiation dependent raft culture system. We wished to correlate this data with cell cycle changes which occur upon AAV2 superinfection of HPV infected cells. Under normal conditions HPV oncogenes E6 and E7 deregulate the expression and function of the tumor suppressors p53 and Rb respectively. Since AAV2 positively targets cells expressing viral oncogenes, we wished to determine the effect of cell cycle changes in an HPV positive cell line, which would enable us to correlate this data with the oncosuppression of HPV mediated by AAV2 via inhibition of HPV replication.

Results

Figure 2:
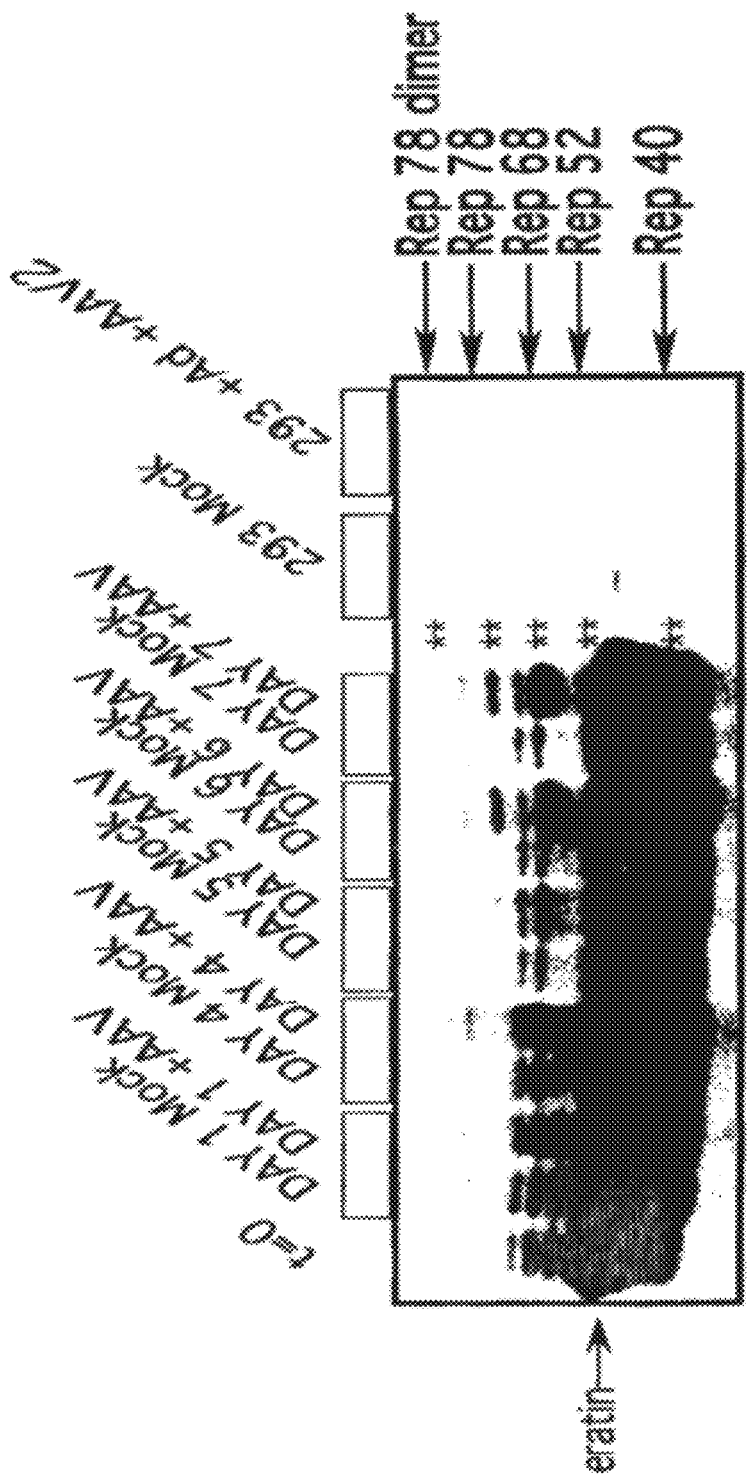
FIG. 2 shows the result of Western Blot analysis of cell extracts showing expression of the four AAV2 Rep proteins Rep78, Rep68, Rep52 and Rep40 late in the infection stage.
Figure 3:
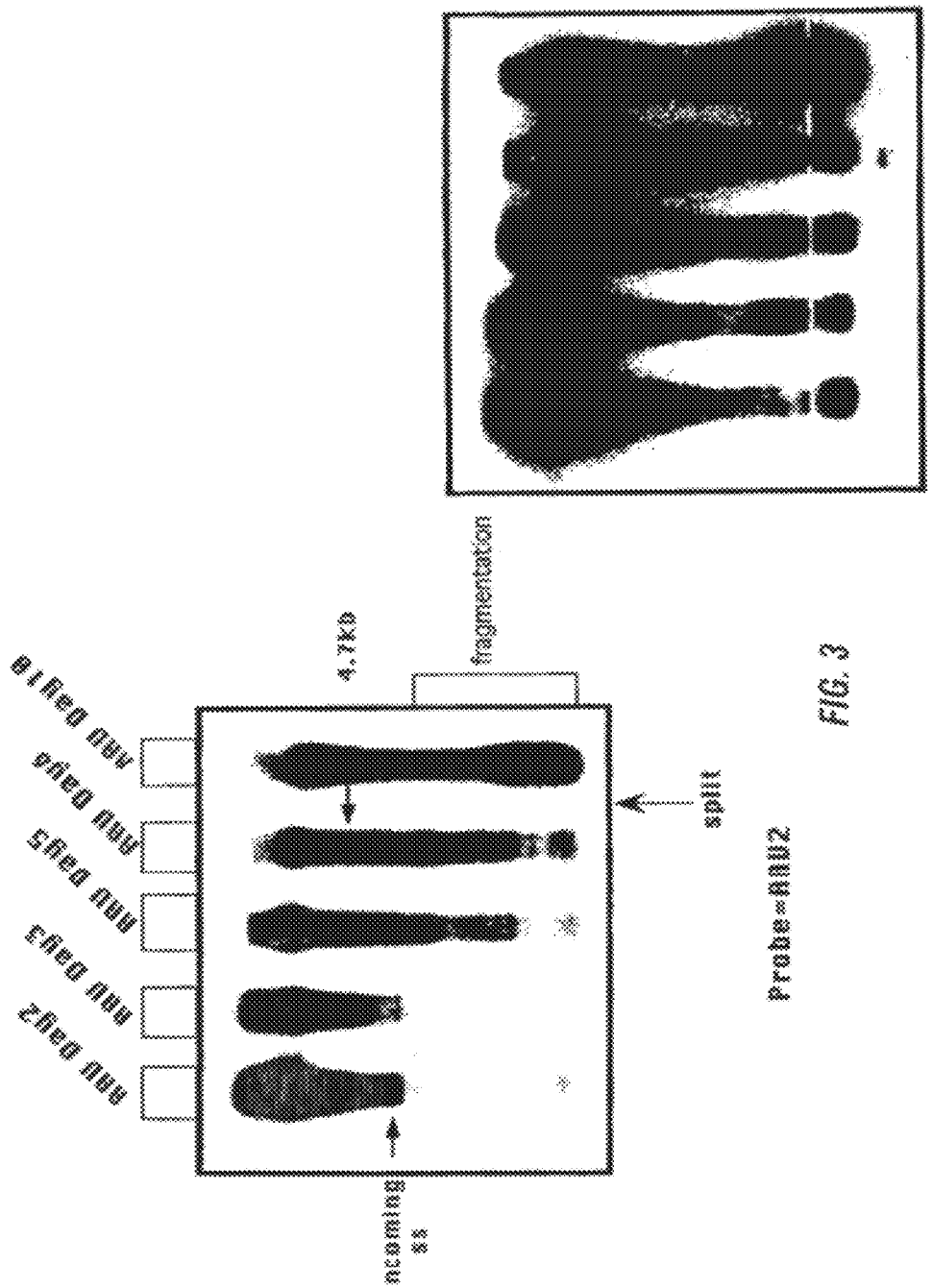
FIG. 3 shows the results of Southern Blot analysis, demonstrating that AAV2 replicated weakly in the AAV2 infected cells as evidenced by the lack of the 4.7 kb replicative monomer.
Figure 4:
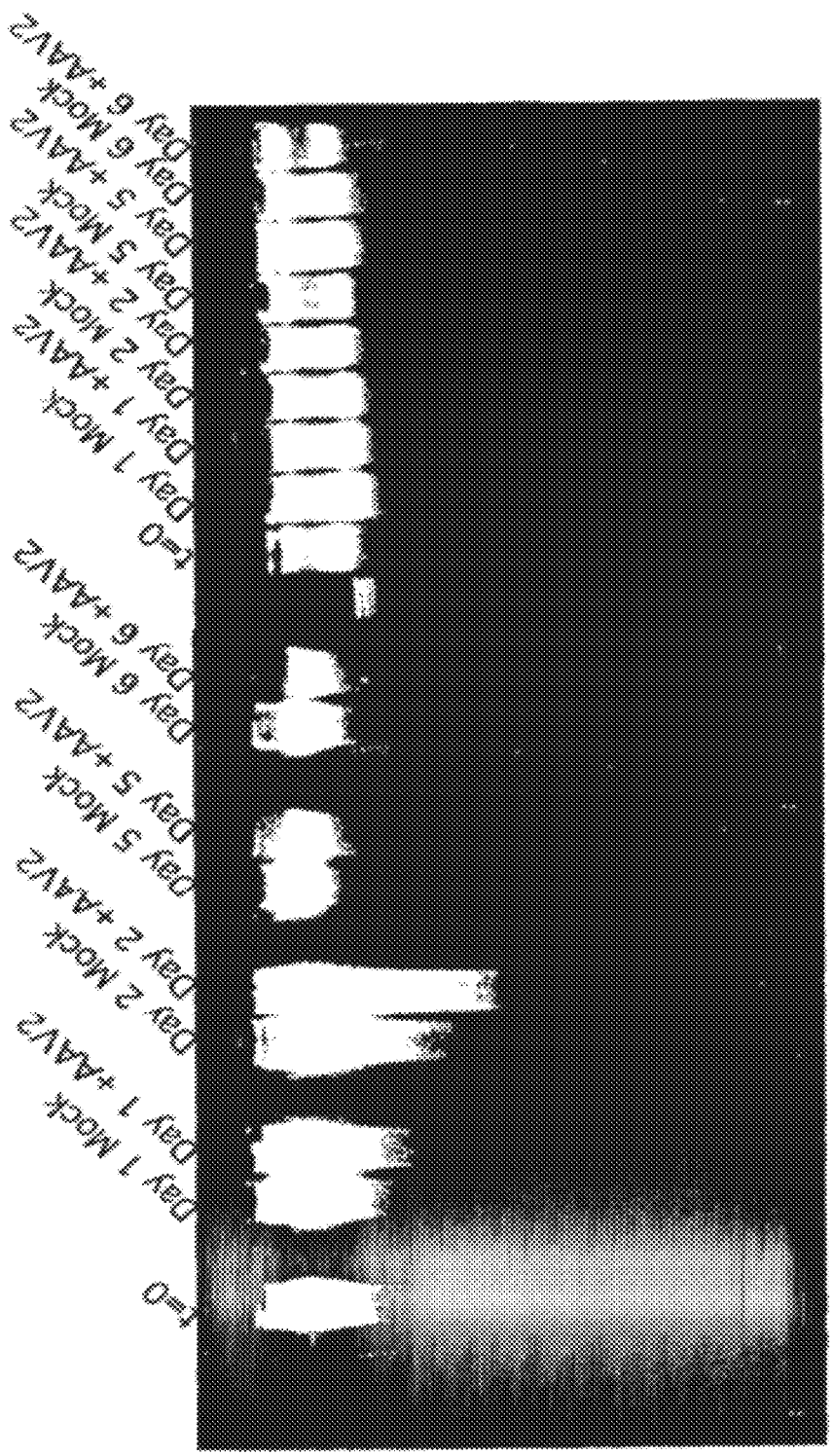
FIG. 4 shows Hirt DNA extraction from the mock infected and AAV2 infected cells and DNA fragmentation analysis. AAV2 infected CIN-612 9E cells underwent significant apoptosis as evidenced by DNA fragmentation analysis. But normal noncancerous cells were unaffected.

We infected subconfluent CIN-612 9E monolayer cell cultures with AAV2 and cultured them over a period of 7 days. The cells were split on Day 2 and Day 4, approximately at the times when the cells were 80% confluent. On Day 6 and Day 7 we visually observed extensive cell death among the AAV2 superinfected CIN-612 9E cells. At this stage, FACS analysis of the mock and AAV2 infected cells suggested that massive cell death was accompanied by a more than 20% increase in the number of cells with S phase DNA content (FIG. 1). We wanted to determine whether the AAV2 mediated cell death could be correlated with AAV2 encoded nonstructural Rep protein expression. Therefore, we performed Western blot analysis of cell extracts from the mock and AAV2 infected CIN-612 9E cells. We observed quantitative expression of the four AAV2 Rep proteins Rep78, Rep68, Rep52 and Rep40 late in the infection stage (FIG. 2). We performed Southern blot analysis to determine the status of AAV2 replication utilizing an AAV2 specific probe. AAV2 replicated weakly in the AAV2 infected cells as evidenced by the lack of the 4.7 kb replicative monomer (FIG. 3). This southern probe also bound to low molecular weight bands. The detection of these fragmented bands was suggestive of apoptosis. In order to determine whether AAV2 infection mediated an apoptotic response in the CIN-612 9E cell line, we performed Hirt DNA extraction from the mock infected and AAV2 infected cells and carried out a DNA fragmentation analysis (FIG. 4). AAV2 infected CIN-612 9E cells underwent significant apoptosis as evidenced by DNA fragmentation analysis, whereas we were unable to detect apoptosis in the mock infected controls. As an additional control, an identical experiment was performed utilizing primary human foreskin keratinocytes. We compared mock infected and AAV2 infected keratinocytes in a similar DNA fragmentation assay. Interestingly, primary human foreskin keratinocytes infected with AAV2 showed no such apoptotic response, suggesting that the AAV2 mediated apoptosis was specific to the HPV3 1b containing cell line.

Figure 5:
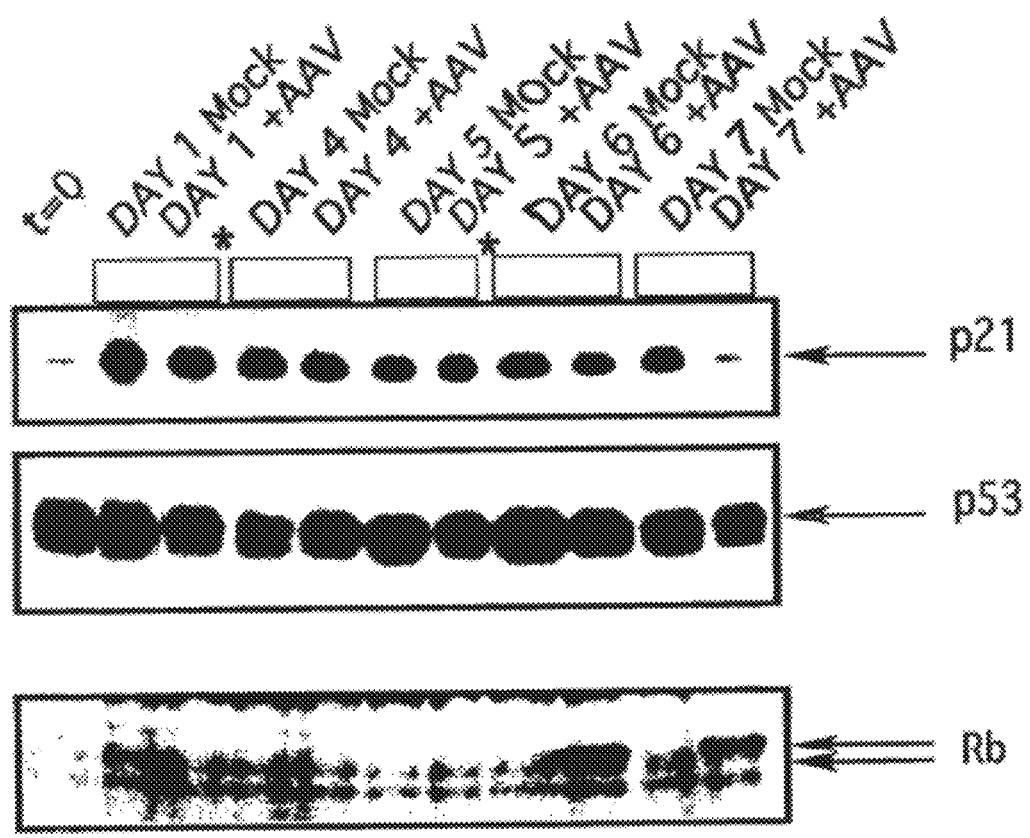
FIG. 5 is an agarose gel electrophoresis showing that AAV2 mediated apoptosis in the CIN-612 9E cells could be correlated with a consistent decrease in p21 levels as well as a decrease in tumor suppressor p53 levels.

AAV2 mediated apoptosis in the CI-612 9E cells could be correlated with a consistent decrease in p21 levels as well as a decrease in tumor suppressor p53 levels (FIG. 5). Interestingly, expression of the Rb tumor suppressor was significantly upregulated and stabilized, suggesting that AAV2 infection significantly modulates HPV3 1b E7 activity or expression of the E7 transcript from the HPV3 1b early promoter. In addition, Rb was predominantly present in its hyperphosphorylated form (FIG. 5). The data presented in FIG. 5 demonstrating AAV2 mediated Rb hyper-phosphorlation correlates with our FACS analysis which indicated that many of the AAV infected cells had died with an S phase DNA content (FIG. 1).

Significance of Observed Results

AAV2 is a ubiquitous, non-pathogenic virus and as such is part of the normal flora of the human anogenital region. Thus, selective positioning of AAV in the same tissue infected by HPV places AAV2 in a unique position to inhibit HPV infections and viral DNA replication. Our results suggest that AAV2 selectively mediates apoptosis as a mode of oncosuppression in the HPV3 1b positive cell line, but not in primary human foreskin keratinocyte lines. These results are consistent with the idea that an ideal cancer therapeutic agent would specifically target tumor cells while leaving the surrounding healthy cells intact. Our results suggest that such an ideal situation could be achieved utilizing the wild-type AAV2 infectious particles and suggest a unique method for the gene therapy of cervical cancer.

Example 2

We had previously demonstrated that infection with the nonpathogenic adeno-associated virus type 2 (AAV2) induced cell death by apoptosis of cervical cancer cells approximately 6 days post-AAV2 infection. When normal, noncancerous cells are infected by AAV2 the cells do not undergo cell death by apoptosis displaying no cytopathic effects. We have now expanded these findings in the following ways.

1) We now have data to show that AAV2 can induce cell death of cervical cancer cells at all stages of carcinogenic progression: preneoplastic cervical intraepithelial neoplasia I (CIN-1) up to cervical invasive carcinoma cells.

TABLE 1

| CELL LINE | CANCER STAGE REPRESENTED | CELL DEATH |
| --- | --- | --- |
| CIN-612 9E | CIN-I (HPV316) | +++ |
| CIN-612 6E | CIN-II (HPV316) | +++ |
| W12 | CIN-I/II (HPV16) | +++ |
| HPV16 | CIN-I (HPV16) | +++ |
| RECA | INVASIVE CARCINOMA (HPV16) | +++ |
| HPV18 | CIN-I (HPV18) | +++ |
| AWCA | INVASIVE CARCINOMA(HPV18) | +++ |
| C33A | INVASIVE CARCINOMA (no HPV) | +++ |
| HFK | NORMAL KERATINOCYTE | NO |

+++ = 100% cell death
++ = 50-75% cell death
+ = 25-50% cell death.

2) We now have data to show that keratinocytes that are immortalized, representing the initial stages of carcinogenic progression, die following infection with AAV2 with kinetics similar to cervical cancer cells.

TABLE 2

| CELL LINE | CANCER STAGE REPRESENTED | CELL DEATH |
| --- | --- | --- |
| N-TERTS | IMMORTALIZED | + |
| NIKS | IMMORTALIZED | +++ |
| HaCats | IMMORTALIZED | +++ |

3) We now have data to show that cancers besides cervical cancer can be induced to die following infection by AAV2.

TABLE 3

| CELL LINE | CANCER TYPE | CELL DEATH |
| --- | --- | --- |
| SCC | Squamous cell carcinoma | +++ |
| MCF-7 | Breast carcinoma | +++ |
| PC-3 | Prostate carcinoma | ++ |
| UACC-903 | Melanoma | + |

We now have reproducible results showing 100% killing.

When these experiments were initiated our primary goals were to investigate the effects of AAV2 on cell cycle regulatory proteins in HPV-infected cervical cancer cells. Studies reported elsewhere have shown that AAV2 mediates a G1 specific cell cycle block in primary fibroblasts. When cell death was observed by apoptosis, a large number entered S-phase and could be correlated with AAV2 Rep protein expression. In addition, multiple studies have demonstrated that the AAV2 encoded Rep78 protein inhibits transcription from both viral and cellular promoters. Neither of these studies showed any data that would imply that AAV2 was causing any effects associated with cell death. We initially studied the effects of AAV2 infection of cervical cancer cells up to 24 hours post-AAV2 infection. We then thought it would be interesting to observe time points beyond the initial 24 hours endpoint. Some plates were allowed to grow for 6-7 days post-AAV2 infection. During this process cells were passaged twice when cells reached 80% confluency. We observed that all the cells on the plate that had been infected with AAV2 had died. Our initial thought was that this was just a chance happening and that something was just wrong with that plate of cells. We had not expected cell death to occur and had no reason to think that it would happen. Using the CIN-612 9E cell line we have now repeated this observation a total of 15 times with the same result, with repeated passaging, at 6-7 days post-AAV2 infection the cervical cells all undergo cell death. Further analysis has shown that cell death was by an apoptotic pathway, as determined by DNA laddering studies. In addition, AAV2 rep proteins were concurrently expressed which can be correlated with cell death.

Example 3

Figure 6:
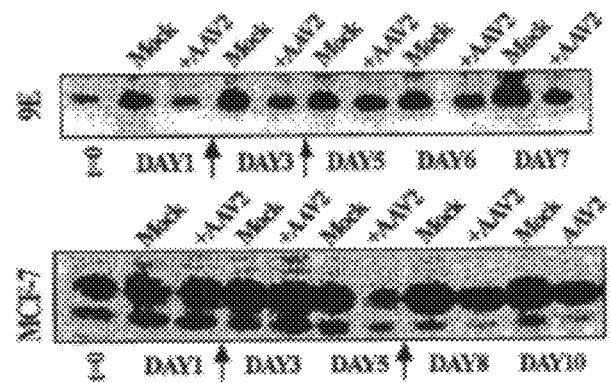
FIG. 6 shows the Western Blot analysis of Monolayer 9E and MCF-7 cells were infected with AAV2 at t=0. Cells were collected over a 7 day period, total proteins extracted, followed by western blot analysis using a polyclonal antibody against $p21^{WAF1}$. Arrows indicate times when cells were passaged upon confluency.

We previously observed that $p21^{WAF1}$ protein levels were downregulated in response to AAV2 infection in CIN-612 9E cells which maintain episomal copies of HPV3 1b. This result is interesting in light of the fact that the $p21^{WAF1}$ protein plays a central role in the induction of apoptosis. Lowering of $p21^{WAF1}$ protein level is a priming step for the apoptosis cascade. We now present results to shown that $p21^{WAF1}$ levels are also decreased in AAV2 infected MCF-7 breast cancer cells. FIG. 6 depicts this observation. Our results indicate that AAV2 mediated apoptosis in these two cancer lines may target similar pathways. The results are shown in FIG. 6. Monolayer 9E and MCF-7 cells were infected with AAV2 at t=0. Cells were collected over a 7 day period, total proteins extracted, followed by western blot analysis using a polyclonal antibody against $p21^{WAF1}$. Arrows indicate times when cells were passaged upon confluency.

Figure 7:
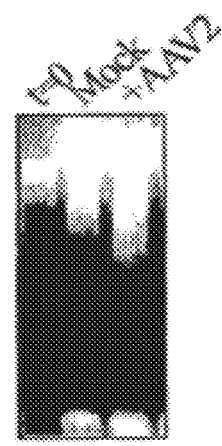
FIG. 7 is an autoradiogram showing the results of extraction of low molecular weight DNA and gel electrophoresis. DNA laddering was evident in AAV2 infected samples.

We have also previously observed that AAV2 infected CIN-612 9E cells undergo apoptotic cell death as evidenced by DNA laddering. We also detected DNA laddering in AAV2 infected MCF-7 cells. The results are shown in FIG. 7. Mock and AAV2 infected MCF-7 cells were harvested followed by extraction of low molecular weight DNA and agarose gel electrophoresis. DNA laddering was evident in AAV2 infected samples.

Figure 8:
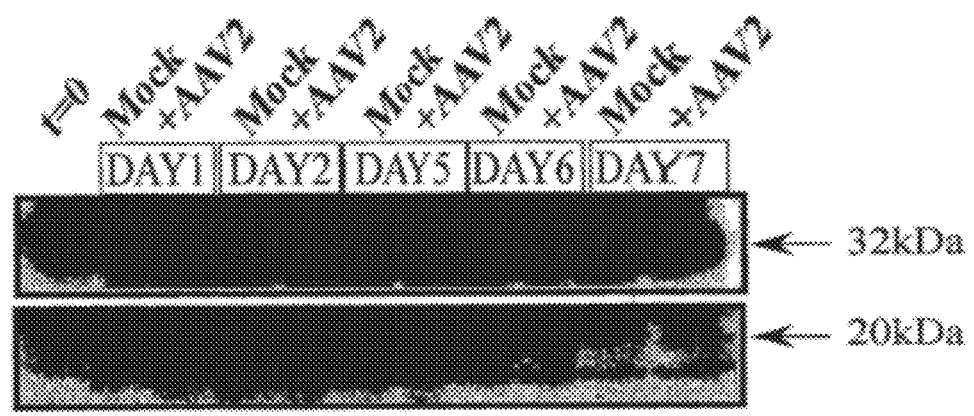
FIG. 8 shows the results of Western Blot analysis of a polyclonal antibody against Caspase-3 on monolayer CIN-612 9E cells infected with AAV2 at t=0. Cells were collected over a 7 day period, total proteins extracted, followed by western blot analysis. The 32 kDa holoenzyme was cleaved to its active form as depicted by the 20 kDa proteolytic fragment.

We further wanted to correlate apoptotic DNA laddering with activity of proteins involved in the execution of apoptosis. Since Caspase-3 is one of the last proteins to be activated in this cascade we performed western blots to look for evidence of Caspase-3 activation. We found that Caspase-3 was cleaved to its active form in AAV2 infected CIN-612 9E cells. The results are depicted in FIG. 8: Monolayer CIN-612 9E cells were infected with AAV2 at t=0. Cells were collected over a 7 day period, total proteins extracted, followed by western blot analysis using a polyclonal antibody against Caspase-3. The 32 kDa holoenzyme was cleaved to its active form as depicted by the 20 kDa proteolytic fragment.

Cumulatively, so far our data indicates that AAV2 mediated regulation of cell cycle proteins couple with downstream pathways which control apoptosis.

Example 4

Figure 9:
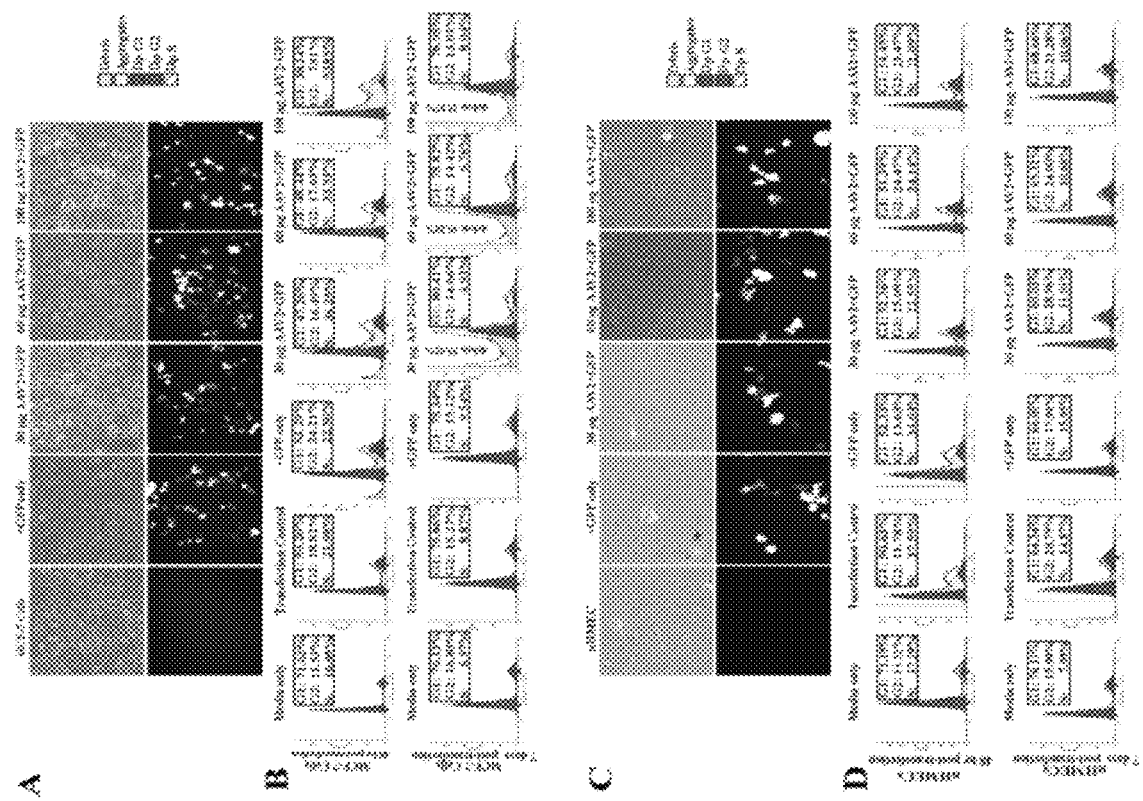
FIG. 9 depicts calcium-phosphate transfection of the cloned AAV2 genome into MCF-7 cells and NHMECs. (A) MCF-7 cells. Untransfected cells, GFP-only controls (+GFP), and GFP vector and AAV2 genome co-transfected cells (+GFP/+AAV2). All images were captured with a 20× objective. (B) MCF-7 cells. Fluorescent Activated Cell Sorting (FACS) Analysis of transfected cells analyzed at 48 h and 7 days post-transfection. Percentages of different cell cycle phases are represented in the G1, S and G2 fractions. Percentage denoting "Debris" is indicative of DNA damage induced cell death/loss of membrane integrity. (C) nHMECs. Untransfected cells, GFP-only controls (+GFP), and GFP vector and AAV2 genome cotransfected cells (+GFP/+AAV2). All images were captured with a 20× objective. (D) nHMECs. Fluorescent Activated Cell Sorting (FACS) Analysis of transfected cells analyzed at 48 h and 7 days post-transfection. Percentages of different cell cycle phases are represented in the G1, S and G2 fractions.

We have observed that the wild-type AAV2 virus infected MCF7 breast cancer cell line (in addition to other grades of breast cancer derived cell lines) undergo apoptotic cell death in which 100% of infected cells die over a 7 day period. In contrast AAV2 failed to productively infect human mammary epithelial cells (nHMECs) and induce apoptosis. Forced delivery of the AAV2 genome into nHMECs using transfection methods failed to induce cell death (FIG. 9D), whereas MCF7 cells similarly transfected underwent cell death as evidenced from the appearance of damaged cell membranes on day 7 post-transfection (FIG. 9B, lower panel).

Forced delivery of the AAV2 genome into MCF7 cells at 48 h post-transfection resulted in increased movement of the cells into the S phase of the cell cycle, similar to what is seen in the wild-type AAV2 infected cells (FIG. 9B). These results along with others have suggested that triggering increased S phase entry induced by AAV2 is the mechanism which further activates downstream cell death pathways. These results correlate with the activation of the observed cell death on day 7 (FIG. 9B, upper panel). Forced delivery of the AAV2 genome into nHMECs failed to induce increased S phase entry or appearance of damaged cell membranes via cell death triggering (FIG. 9D).

It was of interest to find out whether individual AAV2 Rep proteins could trigger the increased S phase entry and the downstream cell death process in the breast cancer cells. We used the Rep78 and Rep68 expression vectors.

Figure 10:
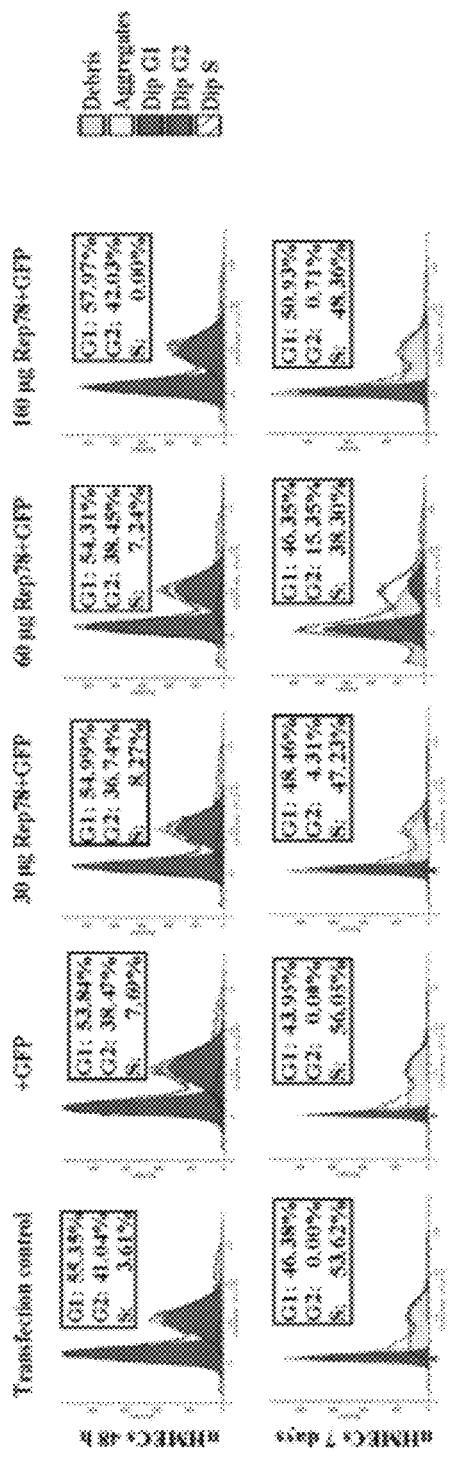
FIG. 10 illustrates the ability of nHMECs to undergo chemically induced and Rep78 induced apoptosis. Calcium-phosphate transfection of the cloned Rep78 expression construct under CMV promoter control into nHMECs. Untransfected control, GFP-only controls (+GFP), and GFP vector and CMV-Rep78 construct cotransfected cells (+GFP/Rep78). Top panel denotes histograms of the DNA distribution representing percentages of cells in the G1, S and G2/M phases of the cell cycle denoted in the bottom panel, as determined using the Cell Quest program of Becton Dickinson. Data were analyzed with the Mod Fit LT program. Analysis of transfected cells analyzed at 48 h and 7 days post-transfection.
Figure 11:
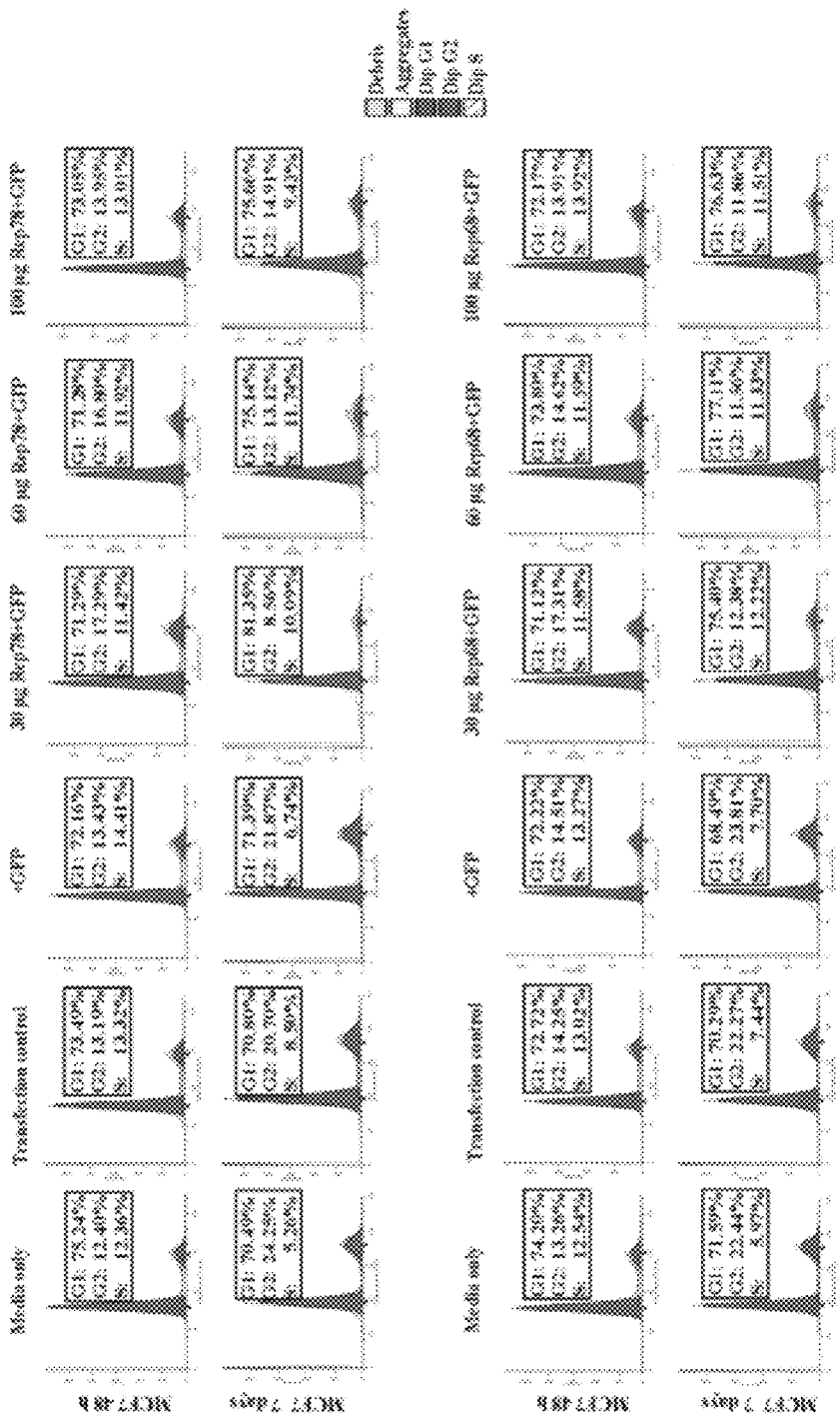
FIG. 11 shows cell cycle analysis of MCF7 cells post-transfection with AAV2 and Rep78 and Rep68 protein expression constructs.

Transfection of Rep 78 alone into nHMECs did not induce either increased S phase entry at 48 h post-transfection or the appearance of damaged membranes on day 7 (FIG. 10). In contrast transfection of either Rep78 and Rep68 alone induced delayed but increased entry of the transfected MCF7 cells into S phase on day 7 but was not associated with the appearance of damaged membranes which would indicate activation of cell death (FIG. 11). In contrast, no significant changes in cell cycle were noted at 48 h post-transfection. These results suggest that each Rep protein alone is sufficient to induce delayed increased S phase entry but not cell death in MCF7 cells, but not in normal cells. These results also suggest that at least two of the AAV2 Rep proteins (Rep78 and Rep 68) potentially work in concert with each other to mediate execution of cell death.

Materials and Methods

We have previously observed that the wild-type AAV2 virus failed to productively infect nHMECs and induce apoptosis, whereas the AAV2 infected MCF7 breast cancer cell line underwent apoptotic cell death, in which a 100% of the cells died in vitro. We also observed the effect of physically delivering the full-length AAV2 genome into nHMECs using standard calcium phosphate DNA co-precipitation and transfection protocols. We have previously utilized this method to show that transfection of the AAV2 genome into HPV positive cells resulted in cell death, whereas normal human keratinocytes similarly transfected were unaffected.

We transfected 30, 60 and 100 µg of either the full-length cloned AAV2 genome into the nHMECs and MCF-7 cells. The same AAV2 clone was also used for production of the AAV2 virus stocks. To determine the transfection efficiency, we also co-transfected 30 µg of a green fluorescent protein (GFP) expression vector (Clontech) as a surrogate marker for the delivery of the unlabeled AAV2 genome into the two cell types. In our hands, the efficiency of the transfection protocol performed with 30 µg of the GFP expression vector alone routinely resulted in an average of 20% of each cell type being GFP positive (FIGS. 9A and 9C), which is within the efficiency range reported for keratinocytes in published studies. At 48 h post-transfection, both the MCF-7 cells and nHMECs co-transfected with the AAV2 genome/GFP expression vector expressed numbers of GFP-positive cells that were approximately equal to the number of cells in each respective type expressing GFP alone (FIGS. 9A and 9C). At this time point, growth/adherence of the AAV2-transfected MCF-7 cells and nHMECs was similar to the GFP only control transfected cells (FIG. 9A). These results are in contrast to our earlier findings which showed cell death of the AAV2-transfected HPV cells at 48 h post-transfection but not the primary human keratinocytes.

An alternative possibility was that AAV2 transfection of breast epithelial cells result in delayed cellular effects which required incubations beyond the 48 h time-point post-transfection, or that a 20% transfection efficiency does not give a strong enough signal which is visualized with this assay. To further determine whether AAV2 transfection into the MCF-7 cells and nHMECs resulted in identifiable early and late changes, we performed cell cycle analysis. We have previously observed the ability of AAV2 infection to modulate the cell cycle machinery in cervical cancer cells at both early and late times post-infection. We determined the percentage distribution of the AAV2 genome transfected MCF-7 and nHMECs in G1, S, G2 and M phases of the cell cycle at 48 h and 7 days post-transfection. At 48 hr post-transfection, AAV2 transfected MCF-7 cells showed a sustained increase in the percentage of cells with S phase DNA content compared to control transfected—as well as GFP only-transfected cells (FIG. 9B). In contrast, at 7 days post-transfection, the percentage of MCF-7 cells in S phase was similar to controls (FIG. 9B), but an increased percentage of dead cells (approximately 25%-30%) was indicated by the appearance "debris", essentially composed of damaged cell membranes which weakly stain with propidium iodide as a result of DNA loss. Therefore, detection of damaged cellular membranes was a measurable consequence of AAV2 induced cell death.

In contrast, at 48 h post-transfection, AAV2 transfected nHMECs displayed S phase fraction of cells which was similar to control transfected cells (FIG. 9D), and these levels did not change after 7 days post-transfection (FIG. 9D). Additionally, AAV2 induced cellular membrane damage ("debris") was not observed at either 48 h or 7 day time-points post-transfection in normal cells (compare FIG. 9B with FIG. 9D). Our results cumulatively suggest that although AAV2 is capable of infecting nHMECs it is unable to establish a persistent infection. These results essentially duplicated our earlier observations that AAV2 was unable to establish a persistent infection in primary keratinocytes. The observed differences are potentially due to sensitivities of the cancer lines to AAV2 mediated gene transcription compared with primary cells.

We also analyzed the ability of transfected Rep78 protein expression construct to induce cell death of nHMECs. For these experiments, 30, 60 and 100 µg of the Rep78 expression vector under control of the CMV promoter was transfected into nHMECs. We performed FACS analysis of the transfected cells both at 48 h and 7 days post-transfection. Neither early or late time points post-transfection showed the ability of Rep78 to induce cell death to any measurable degree (FIG. 10) (and compare FIG. 9 with FIG. 10). The inability of Rep78 to induce cell death of nHMECs could suggest the possibility that Rep78 alone is insufficient for death induction and perhaps the other Rep proteins need to be co-expressed for apoptosis to occur. In contrast, transfection of either the Rep78 and Rep68 protein expression constructs into the MCF7 breast cancer cell line induced a 50% increase in the number of cells undergoing S phase (although delayed) entry at 7 days post-transfection compared with controls (FIG. 11). Additionally, Rep78 and Rep68 induced S phase entry of MCF7 cells but could not be correlated with the appearance of damaged cell membranes (FIG. 11). No significant changes in the cell cycle progression were noted at 48 h post-transfection (FIG. 11). Our results suggest that expression of either the Rep78 or Rep68 protein alone was sufficient for increased S phase entry, but not cell death as would be indicated by the appearance of damaged membranes. Our previous observations have suggested that AAV2 infection triggered entry into S phase is potentially the initial mechanism which activates the cell death pathways. Our new data suggest that Rep78 and Rep68 potentially need to work in concert to achieve the cell killing observed with the wild-type AAV2.

Transfection Assays

MCF7 cells were transfected using the calcium phosphate method as previously described. Both N,N-bis(2-hydroxyethyl)-2-aminoethane-sulfonic acid (BES) and CaCl2 were purchased from Sigma-Aldrich. Briefly, a stock solution of 2.5 M CaCl2 was prepared and filter sterilized through a 0.22 µm filter, and stored at −20° C. A stock solution of 2×BES-buffered saline (2× BBS) was prepared containing 50 mM BES, 280 mM NaCl, and 1.5 mM Na2HPO4. The pH was adjusted to pH 6.95 with HCl, filter sterilized through a 0.22 µm filter and stored at −20° C. Cells were seeded 24 h prior to transfection using 106 cells per 100-mm dish in E-medium containing 5% FBS without the addition of antibiotics. The mixture for transfecting cells was prepared as follows: 30, 60 and 100 µg of the plasmid containing the full-length AAV2 Rep78 and Rep 68 protein expression constructs was added to deionized water up to a volume of 450 µl, followed by addition of 50 µl of 2.5 mM CaCl2. Finally, 500 µl of 2× BBS was added to this mixture, mixed gently, followed by incubation at room temperature for 10-20 min. To determine the transfection efficiency, 30 µg of a green fluorescent protein (GFP) expression vector (Clontech) was transfected alone or co-transfected with the AAV2 genome into cells and used as a surrogate marker for delivery of the unlabeled AAV2 plasmid DNA where indicated. Transfection controls were essentially cells treated with the calcium phosphate precipitate without the addition of plasmid DNA. The 1 ml DNA suspension was mixed by gently inverting and added to the 100 mm culture dishes dropwise, followed by swirling the plates to evenly distribute the DNA precipitate. Following 24 hr of incubation, the medium was removed and cultures were rinsed twice using E-medium without serum and finally replaced with E-medium supplemented with 5% FBS without antibiotics and incubation was further continued for 24 hr. These samples were designated as the 48 hr samples post-transfection. Another set of cells was further incubated for 5 days and designated as the 7 day samples post-transfection. At the end of the designated incubation times cells were harvested by trypsinization, washed with phosphate-buffered saline (PBS) and fixed in 70% ethanol and prepared for FACS analysis.

Example 5 Sequences

Example 5

AAV2 and Death Induction of HPV Positive Oral Cells

In addition to the multiple cancer lines already tested, Applicants have obtained data with human tonsil cells. Applicants generated human tonsil cell lines maintaining episomal copies of HPV16 which are capable of producing infectious virus in three-dimensional tissues. This cell line is therefore a representative model for head and neck cancers. Applicants tested the ability of AAV2 to infect and induce cell death of these HPV16-positive tonsil cells. AAV2 also induced death of these cells in culture, over a period of seven days, as characteristic of most of the other cancer lines we have tested.

Example 6 Sequences

```
Rep68 DNA Coding Sequence in AAV2 Genome
                                                           SEQ ID NO: 1
    Join (nt. 321 . . . 1906, nt. 2228. . . 2252)
      1 ttggccactc cctctctgcg cgctcgctcg ctcactgagg ccgggcgacc aaaggtcgcc 61 cgacgcccgg gctttgcccg ggcggcctca gtgagcgagc gagcgcgcag agagggagtg 121 gccaactcca tcactagggg ttcctggagg ggtggagtcg tgacgtgaat tacgtcatag 181 ggttagggag gtcctgtatt agaggtcacg tgagtgtttt gcgacatttt gcgacaccat 241 gtggtcacgc tgggtattta agcccgagtg agcacgcagg gtctccattt tgaagcggga 301 ggtttgaacg cgcagccgcc atgccggggt tttacgagat tgtgattaag gtccccagcg 361 accttgacga gcatctgccc ggcatttctg acagctttgt gaactgggtg gccgagaagg 421 aatgggagtt gccgccagat tctgacatgg atctgaatct gattgagcag gcaccctga 481 ccgtggccga gaagctgcag cgcgactttc tgacggaatg gcgccgtgtg agtaaggccc 541 cggaggccct tttctttgtg caatttgaga agggagagag ctacttccac atgcacgtgc 601 tcgtggaaac caccgggtg aaatccatgg ttttgggacg tttcctgagt cagattcgcg 661 aaaaactgat tcagagaatt taccgcggga tcgagccgac tttgccaaac tggttcgcgg 721 tcacaaagac cagaaatggc gccggaggcg ggaacaaggt ggtggatgag tgctacatcc 781 ccaattactt gctccccaaa acccagcctg agctccagtg ggcgtggact aatatggaac 841 agtatttaag cgcctgtttg aatctcacgg agcgtaaacg gttggtggcg cagcatctga 901 cgcacgtgtc gcagacgcag gagcagaaca aagagaatca gaatcccaat tctgatgcgc 961 cggtgatcag atcaaaaact tcagccaggt acatggagct ggtcgggtgg ctcgtggaca
```

-continued

```
1021 aggggattac ctcggagaag cagtggatcc aggaggacca ggcctcatac atctccttca
1081 atgcggcctc caactcgcgg tcccaaatca aggctgcctt ggacaatgcg ggaaagatta
1141 tgagcctgac taaaaccgcc cccgactacc tggtgggcca gcagcccgtg gaggacattt
1201 ccagcaatcg gatttataaa attttggaac taaacgggta cgatcccaa tatgcggctt
1261 ccgtcttct gggatgggcc acgaaaaagt tcggcaagag gaacaccatc tggctgtttg
1321 ggcctgcaac taccgggaag accaacatcg cggaggccat agcccacact gtgcccttct
1381 acgggtgcgt aaactggacc aatgagaact ttcccttcaa cgactgtgtc gacaagatgg
1441 tgatctggtg ggaggagggg aagatgaccg ccaaggtcgt ggagtcggcc aaagccattc
1501 tcggaggaag caaggtgcgc gtggaccaga aatgcaagtc ctcggcccag atagacccga
1561 ctcccgtgat cgtcacctcc aacaccaaca tgtgcgccgt gattgacggg aactcaacga
1621 ccttcgaaca ccagcagccg ttgcaagacc ggatgttcaa atttgaactc acccgccgtc
1681 tggatcatga ctttgggaag gtcaccaagc aggaagtcaa agactttttc cggtgggcaa
1741 aggatcacgt ggttgaggtg gagcatgaat tctacgtcaa aaagggtgga gccaagaaaa
1801 gacccgcccc cagtgacgca gatataagtg agcccaaacg ggtgcgcgag tcagttgcgc
1861 agccatcgac gtcagacgcg gaagcttcga tcaactacgc agacag gtac caaaacaaat
1921 gttctcgtca cgtgggcatg aatctgatgc tgtttccctg cagacaatgc gagagaatga
1981 atcagaattc aaatatctgc ttcactcacg gacagaaaga ctgtttagag tgctttcccg
2041 tgtcagaatc tcaacccgtt tctgtcgtca aaaaggcgta tcagaaactg tgctacattc
2101 atcatatcat gggaaaggtg ccagacgctt gcactgcctg cgatctggtc aatgtggatt
2161 tggatgactg catctttgaa caataaatga tttaaatcag gtatggctgc cgatggttat
2221 cttccag att ggctcgagga cactctctct ga aggaataa cagtggtg gaagctcaaa
2281 cctggcccac caccaccaaa gcccgcagag cggcataagg acgacagcag gggtcttgtg
2341 cttcctgggt acaagtacct cggacccttc aacggactcg acaagggaga gccggtcaac
2401 gaggcagacg ccgcggccct cgagcacgac aaagcctacg accggcagct cgacagcgga
2461 gacaacccgt acctcaagta caaccacgcc gacgcggagt tcaggagcg ccttaaagaa
2521 gatacgtctt ttgggggcaa cctcggacga gcagtcttcc aggcgaaaaa gagggttctt
2581 gaacctctgg gcctggttga ggaacctgtt aagacggctc cgggaaaaaa gaggccggta
2641 gagcactctc ctgtggagcc agactcctcc tcgggaaccg gaaaggcggg ccagcagcct
2701 gcaagaaaaa gattgaattt tggtcagact ggagacgcag actcagtacc tgaccccag
2761 cctctcggac agccaccagc agcccctct ggtctgggaa ctaatacgat ggctacaggc
2821 agtggcgcac caatgcaga caataacgag gcgccgacg gagtgggtaa ttcctcggga
2881 aattggcatt gcgattccac atggatgggc gacagagtca tcaccaccag cacccgaacc
2941 tgggccctgc ccacctacaa caaccacctc tacaaacaaa tttccagcca atcaggagcc
3001 tcgaacgaca atcactactt tggctacagc accccttggg ggtattttga cttcaacaga
3061 ttccactgcc acttttcacc acgtgactgg caaagactca tcaacaacaa ctggggattc
3121 cgacccaaga gactcaactt caagctcttt aacattcaag tcaaagaggt cacgcagaat
3181 gacggtacga cgacgattgc caataacctt accagcacgg ttcaggtgtt tactgactcg
3241 gagtaccagc tcccgtacgt cctcggctcg gcgcatcaag gatgcctccc gccgttccca
3301 gcagacgtct tcatggtgcc acagtatgga tacctcaccc tgaacaacgg gagtcaggca
3361 gtaggacgct cttcatttta ctgcctggag tactttcctt ctcagatgct gcgtaccgga
3421 aacaactta ccttcagcta cacttttgag gacgttcctt tccacagcag ctacgctcac
```

```
3481 agccagagtc tggaccgtct catgaatcct ctcatcgacc agtacctgta ttacttgagc 3541 agaacaaaca ctccaagtgg aaccaccacg cagtcaaggc ttcagttttc tcaggccgga 3601 gcgagtgaca ttcgggacca gtctaggaac tggcttcctg gaccctgtta ccgccagcag 3661 cgagtatcaa agacatctgc ggataacaac aacagtgaat actcgtggac tggagctacc 3721 aagtaccacc tcaatggcag agactctctg gtgaatccgg gcccggccat ggcaagccac 3781 aaggacgatg aagaaaagtt ttttcctcag gcgggttc tcatctttgg gaagcaaggc 3841 tcagagaaaa caaatgtgga cattgaaaag gtcatgatta cagacgaaga ggaaatcagg 3901 acaaccaatc ccgtggctac ggagcagtat ggttctgtat ctaccaacct ccagagaggc 3961 aacagacaag cagctaccgc agatgtcaac acacaaggcg ttcttccagg catggtctgg 4021 caggacagag atgtgtacct tcaggggccc atctgggcaa agattccaca cacggacgga 4081 cattttcacc cctctcccct catgggtgga ttcggactta aacaccctcc tccacagatt 4141 ctcatcaaga acaccccggt acctgcgaat ccttcgacca ccttcagtgc ggcaaagttt 4201 gcttccttca tcacacagta ctccacggga caggtcagcg tggagatcga gtgggagctg 4261 cagaaggaaa acagcaaacg ctggaatccc gaaattcagt acacttccaa ctacaacaag 4321 tctgttaatg tggactttac tgtggacact aatggcgtgt attcagagcc tcgccccatt 4381 ggcaccagat acctgactcg taatctgtaa ttgcttgtta atcaataaac cgtttaattc 4441 gtttcagttg aactttggtc tctgcgtatt tctttcttat ctagtttcca tggctacgta 4501 gataagtagc atggcgggtt aatcattaac tacaaggaac ccctagtgat ggagttggcc 4561 actccctctc tgcgcgctcg ctcgctcact gaggccgggc gaccaaaggt cgcccgacgc 4621 ccgggctttg cccgggcggc ctcagtgagc gagcgagcgc gcagagaggg agtggccaa

4679 ----
```

Rep 68 protein

SEQ ID NO: 2

/protein_id = "YP_680422.1"
/db_xref = "GI: 110645917"
/db_xref = "GeneID: 4192013"

MPGFYEIVIKVPSDLDEHLPGISDSFVNWVAEKEWELPPDSDMD

LNLIEQAPLTVAEKLQRDFLTEWRRVSKAPEALFFVQFEKGESYFHMHVLVETTGVKS

MVLGRFLSQIREKLIQRIYRGIEPTLPNWFAVTKTRNGAGGGNKVVDECYIPNYLLPK

TQPELQWAWTNMEQYLSACLNLTERKRLVAQHLTHVSQTQEQNKENQNPNSDAPVIRS

KTSARYMELVGWLVDKGITSEKQWIQEDQASYISFNAASNSRSQIKAALDNAGKIMSL

TKTAPDYLVGQQPVEDISSNRIYKILELNGYDPQYAASVFLGWATKKFGKRNTIWLFG

PATTGKTNIAEAIAHTVPFYGCVNWTNENFPFNDCVDKMVIWWEEGKMTAKVVESAKA

ILGGSKVRVDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDADISEPKRVR

ESVAQPSTSDAEASINYADRLARGHSL

Rep78 DNA Coding Sequence in AAV2 Genome
(nt 321 . . . 2186)

SEQ ID NO: 3

```
  1 ttggccactc cctctctgcg cgctcgctcg ctcactgagg ccgggcgacc aaaggtcgcc 61 cgacgcccgg gctttgcccg ggcggcctca gtgagcgagc gagcgcgcag agagggagtg 121 gccaactcca tcactagggg ttcctggagg ggtggagtcg tgacgtgaat tacgtcatag 181 ggttagggag gtcctgtatt agaggtcacg tgagtgtttt gcgacatttt gcgacaccat 241 gtggtcacgc tgggtattta agcccgagtg agcacgcagg gtctccattt tgaagcggga
```

-continued

```
 301 ggtttgaacg cgcagccgcc atgccggggt tttacgagat tgtgattaag gtccccagcg
 361 accttgacga gcatctgccc ggcatttctg acagctttgt gaactgggtg gccgagaagg
 421 aatgggagtt gccgccagat tctgacatgg atctgaatct gattgagcag gcacccctga
 481 ccgtggccga gaagctgcag cgcgactttc tgacggaatg cgccgtgtg agtaaggccc
 541 cggaggccct tttctttgtg caatttgaga agggagagag ctacttccac atgcacgtgc
 601 tcgtggaaac caccgggtg aaatccatgg ttttgggacg tttcctgagt cagattcgcg
 661 aaaaactgat tcagagaatt taccgcggga tcgagccgac tttgccaaac tggttcgcgg
 721 tcacaaagac cagaaatggc gccggaggcg ggaacaaggt ggtggatgag tgctacatcc
 781 ccaattactt gctccccaaa acccagcctg agctccagtg ggcgtggact aatatggaac
 841 agtatttaag cgcctgtttg aatctcacgg agcgtaaacg gttggtggcg cagcatctga
 901 cgcacgtgtc gcagacgcag gagcagaaca aagagaatca gaatcccaat tctgatgcgc
 961 cggtgatcag atcaaaaact tcagccaggt acatggagct ggtcgggtgg ctcgtggaca
1021 aggggattac ctcggagaag cagtggatcc aggaggacca ggcctcatac atctccttca
1081 atgcggcctc caactcgcgg tcccaaatca aggctgcctt ggacaatgcg ggaaagatta
1141 tgagcctgac taaaaccgcc cccgactacc tggtgggcca gcagcccgtg gaggacattt
1201 ccagcaatcg gatttataaa attttggaac taaacgggta cgatccccaa tatgcggctt
1261 ccgtctttct gggatgggcc acgaaaaagt tcggcaagag gaacaccatc tggctgtttg
1321 ggcctgcaac taccgggaag accaacatcg cggaggccat agcccacact gtgcccttct
1381 acgggtgcgt aaactggacc aatgagaact ttcccttcaa cgactgtgtc gacaagatgg
1441 tgatctggtg ggaggagggg aagatgaccg ccaaggtcgt ggagtcggcc aaagccattc
1501 tcggaggaag caaggtgcgc gtggaccaga atgcaagtc ctcggcccag atagacccga
1561 ctcccgtgat cgtcacctcc aacaccaaca tgtgcgccgt gattgacggg aactcaacga
1621 ccttcgaaca ccagcagccg ttgcaagacc ggatgttcaa atttgaactc acccgccgtc
1681 tggatcatga ctttgggaag gtcaccaagc aggaagtcaa agacttttc cggtgggcaa
1741 aggatcacgt ggttgaggtg gagcatgaat tctacgtcaa aaagggtgga gccaagaaaa
1801 gacccgcccc cagtgacgca gatataagtg agcccaaacg ggtgcgcgag tcagttgcgc
1861 agccatcgac gtcagacgcg gaagcttcga tcaactacgc agacaggtac caaaacaaat
1921 gttctcgtca cgtgggcatg aatctgatgc tgtttccctg cagacaatgc gagagaatga
1981 atcagaattc aaatatctgc ttcactcacg gacagaaaga ctgtttagag tgctttcccg
2041 tgtcagaatc tcaacccgtt tctgtcgtca aaaaggcgta tcagaaactg tgctacattc
2101 atcatatcat ggggaaggtg ccagacgctt gcactgcctg cgatctggtc aatgtggatt
2161 tggatgactg catctttgaa caataaatga tttaaatcag gtatggctgc cgatggttat
2221 cttccagatt ggctcgagga cactctctct gaaggaataa gacagtggtg gaagctcaaa
2281 cctggcccac caccaccaaa gcccgcagag cggcataagg acgacagcag gggtcttgtg
2341 cttcctgggt acaagtacct cggacccttc aacggactcg acaagggaga gccggtcaac
2401 gaggcagacg ccgcggccct cgagcacgac aaagcctacg accggcagct cgacagcgga
2461 gacaacccgt acctcaagta caaccacgcc gacgcggagt tcaggagcg ccttaaagaa
2521 gatacgtctt tgggggcaa cctcggacga gcagtcttcc aggcgaaaaa gagggttctt
2581 gaacctctgg gcctggttga ggaacctgtt aagacggctc cgggaaaaaa gaggccggta
2641 gagcactctc ctgtggagcc agactcctcc tcgggaaccg aaaggcgggg ccagcagcct
2701 gcaagaaaaa gattgaattt tggtcagact ggagacgcag actcagtacc tgaccccag
```

-continued

```
2761 cctctcggac agccaccagc agcccctct ggtctgggaa ctaatacgat ggctacaggc
2821 agtggcgcac aatggcaga caataacgag gcgccgacg gagtgggtaa ttcctcggga
2881 aattggcatt gcgattccac atggatgggc gacagagtca tcaccaccag caccgaacc
2941 tgggccctgc ccacctacaa caaccacctc tacaaacaaa tttccagcca atcaggagcc
3001 tcgaacgaca tcactactt tggctacagc accccttggg ggtattttga cttcaacaga
3061 ttccactgcc acttttcacc acgtgactgg caaagactca tcaacaacaa ctggggattc
3121 cgacccaaga gactcaactt caagctcttt aacattcaag tcaaagaggt cacgcagaat
3181 gacggtacga cgacgattgc caataacctt accagcacgg ttcaggtgtt tactgactcg
3241 gagtaccagc tcccgtacgt cctcggctcg gcgcatcaag gatgcctccc gccgttccca
3301 gcagacgtct tcatggtgcc acagtatgga tacctcaccc tgaacaacgg gagtcaggca
3361 gtaggacgct cttcattta ctgcctggag tactttcctt ctcagatgct gcgtaccgga
3421 aacaacttta ccttcagcta cacttttgag gacgttcctt tccacagcag ctacgctcac
3481 agccagagtc tggaccgtct catgaatcct ctcatcgacc agtacctgta ttacttgagc
3541 agaacaaaca ctccaagtgg aaccaccacg cagtcaaggc ttcagttttc tcaggccgga
3601 gcgagtgaca ttcgggacca gtctaggaac tggcttcctg gaccctgtta ccgccagcag
3661 cgagtatcaa agacatctgc ggataacaac aacagtgaat actcgtggac tggagctacc
3721 aagtaccacc tcaatggcag agactctctg gtgaatccgg gcccggccat ggcaagccac
3781 aaggacgatg aagaaaagtt ttttcctcag agcggggttc tcatctttgg gaagcaaggc
3841 tcagagaaaa caaatgtgga cattgaaaag gtcatgatta cagacgaaga ggaaatcagg
3901 acaaccaatc ccgtgctac ggagcagtat ggttctgtat ctaccaacct ccagagaggc
3961 aacagacaag cagctaccgc agatgtcaac acacaaggcg ttcttccagg catggtctgg
4021 caggacagaa tgtgtacct tcaggggccc atctgggcaa agattccaca cacggacgga
4081 catttttcacc cctctccct catgggtgga ttcggactta acaccctcc tccacagatt
4141 ctcatcaaga cacccggt acctgcgaat ccttcgacca ccttcagtgc ggcaaagttt
4201 gcttccttca tcacacagta ctccacggga caggtcagcg tggagatcga gtgggagctg
4261 cagaaggaaa acagcaaacg ctggaatccc gaaattcagt acacttccaa ctacaacaag
4321 tctgttaatg tggactttac tgtggacact aatggcgtgt attcagagcc tcgccccatt
4381 ggcaccagat acctgactcg taatctgtaa ttgcttgtta atcaataaac cgtttaattc
4441 gtttcagttg aactttggtc tctgcgtatt tctttcttat ctagtttcca tggctacgta
4501 gataagtagc atggcgggtt aatcattaac tacaaggaac ccctagtgat ggagttggcc
4561 actccctctc tgcgcgctcg ctcgctcact gaggccgggc gaccaaaggt cgcccgacgc
4621 ccgggctttg cccggcggc ctcagtgagc gagcgagcgc gcagagaggg agtggccaa-------
4679
```

Rep 78 protein                                                    SEQ ID NO: 4
/protein_id = "YP_680423.1"
/db_xref = "GI: 110645918"
/db_xref = "GeneID: 1489608"
MPGFYEIVIKVPSDLDEHLPGISDSFVNWVAEKEWELPPDSDMD

LNLIEQAPLTVAEKLQRDFLTEWRRVSKAPEALFFVQFEKGESYFHMHVLVETTGVKS

MVLGRFLSQIREKLIQRIYRGIEPTLPNWFAVTKTRNGAGGGNKVVDECYIPNYLLPK

TQPELQWAWTNMEQYLSACLNLTERKRLVAQHLTHVSQTQEQNKENQNPNSDAPVIRS

KTSARYMELVGWLVDKGITSEKQWIQEDQASYISFNAASNSRSQIKAALDNAGKIMSL

-continued

```
TKTAPDYLVGQQPVEDISSNRIYKILELNGYDPQYAASVFLGWATKKFGKRNTIWLFG

PATTGKTNIAEAIAHTVPFYGCVNWTNENFPFNDCVDKMVIWWEEGKMTAKVVESAKA

ILGGSKVRVDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDADISEPKRV

RESVAQPSTSDAEASINYADRYQNKCSRHVGMNLMLFPCRQCERMNQNSNICFTHGQK

DCLECFPVSESQPVSVVKKAYQKLCYIHHIMGKVPDACTACDLVNVDLDDCIFEQ
```

The following resources are incorporated in their entirety by reference, Gen bank Accession number NC_001401, and Marcello et al, Journal of Virology 2000, 74 (19):9090. "Adeno-Associated Virus Type 2 Rep Protein Inhibits Human Papillomavirus Type 16 E2 Recruitment of the Transctipional Coactivator p300" particularly, page 9091 cloumn 1 lines 17-41 describing the construction of expression vectors phisRep68 and phisRep78.

What is claimed is:

1. A method of treating or ameliorating cancer comprising administering to a patient having cancer, a recombinant protein comprising AAV2 Rep68 and AAV2 Rep78, and
   inducing an increase in S-phase entry in cancer cells in said patient,
   wherein said treatment or amelioration of said cancer is performed without inclusion of any additional anti-cancer compound, chemotherapeutic agent, or other DNA damaging agent.

2. The method of claim 1 wherein said protein is administration is by administration of an expression construct comprising a nucleic acid sequence which encodes an AAV2 Rep 68 and Rep 78 protein.

3. The method of claim 1 wherein said protein has an amino acid sequence of SEQ ID NO:2 and 4.

4. The method of claim 2 wherein said nucleic acid sequence encodes the protein of SEQ ID NO:2 and 4.

5. The method of claim 4 wherein said nucleic acid sequence includes the sequence of SEQ ID NO:1 and 3 operable linked to a promoter sequence.

6. The method of claim 1 wherein said protein induces apoptosis.

7. The method of claim 1 wherein said protein is administered as part of a genetically modified AAV2 virus.

8. The method of claim 1 wherein said cancer is breast cancer, cervical, mesothelioma, prostate cancer, squamous cell carcinoma or melanoma.

* * * * *

```
                        SEQUENCE LISTING

<160> NUMBER OF SEQ ID NOS: 4

<210> SEQ ID NO 1
<211> LENGTH: 4679
<212> TYPE: DNA
<213> ORGANISM: adeno-associated virus 2

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacga gcatctgccc ggcatttctg acagctttgt gaactgggtg gccgagaagg     420
aatgggagtt gccgccagat tctgacatgg atctgaatct gattgagcag gcaccctga     480 ccgtggccga gaagctgcag cgcgactttc tgacggaatg gcgccgtgtg agtaaggccc     540 cggaggcect tttctttgtg caatttgaga agggagagag ctacttccac atgcacgtgc     600
tcgtggaaac caccggggtg aaatccatgg ttttgggacg tttcctgagt cagattcgcg     660
aaaaactgat tcagagaatt taccgcggga tcgagccgac tttgccaaac tggttcgcgg     720
tcacaaagac cagaaatggc gccggaggcg ggaacaaggt ggtggatgag tgctacatcc     780
ccaattactt gctccccaaa acccagcctg agctccagtg ggcgtggact aatatggaac     840
agtatttaag cgcctgtttg aatctcacgg agcgtaaacg gttggtggcg cagcatctga     900
cgcacgtgtc gcagacgcag gagcagaaca aagagaatca gaatcccaat tctgatgcgc     960
cggtgatcag atcaaaaact tcagccaggt acatggagct ggtcgggtgg ctcgtggaca    1020 agggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagccgtg gaggacattt    1200 ccagcaatcg gatttataaa attttggaac taaacgggta cgatcccaa tatgcggctt    1260 ccgtcttttc gggatgggcc acgaaaaagt tcggcaagag gaacaccatc tggctgtttg    1320
ggcctgcaac taccggaaag accaacatcg cggaggccat agcccacact gtgcccttct    1380
acgggtgcgt aaactggacc aatgagaact ttcccttcaa cgactgtgtc gacaagatgg    1440
```

```
tgatctggtg ggaggagggg aagatgaccg ccaaggtcgt ggagtcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa     1740
aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg aagctcaaa     2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacc ccgcggccct cgagcacgac aaagcctacg accggcagct cgacagcgga    2460
gacaacccgt acctcaagta caaccacgcc gacgcggagt tcaggagcg ccttaaagaa     2520
gatacgtctt tgggggcaa cctcggacga gcagtcttcc aggcgaaaaa gagggttctt     2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag     2760
cctctcggac agccaccagc agcccctctc ggtctgggaa ctaatacgat ggctacaggc    2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcattta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg gaccctgtta ccgccagcag    3660
cgagtatcaa agacatctgc ggataacaac aacagtgaat actcgtggac tggagctacc    3720
aagtaccacc tcaatggcag agactctctg gtgaatccgg gccggccat ggcaagccac     3780
aaggacgatg aagaaaagtt ttttcctcag agcggggttc tcatctttgg gaagcaaggc    3840
```

-continued

```
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acacccctcc tccacagatt    4140
ctcatcaaga cacccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679
```

<210> SEQ ID NO 2
<211> LENGTH: 536
<212> TYPE: PRT
<213> ORGANISM: adeno-associated virus 2

<400> SEQUENCE: 2

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220
```

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
        260                 265                 270

Ile Met Ser Leu Thr Lys Thr Ala Pro Asp Tyr Leu Val Gly Gln Gln
    275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
        340                 345                 350

Phe Tyr Gly Cys Val Asn Trp Thr Asn Glu Asn Phe Pro Phe Asn Asp
    355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
    435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
        500                 505                 510

Ala Gln Pro Ser Thr Ser Asp Ala Glu Ala Ser Ile Asn Tyr Ala Asp
    515                 520                 525

Arg Leu Ala Arg Gly His Ser Leu
530                 535

<210> SEQ ID NO 3
<211> LENGTH: 4679
<212> TYPE: DNA
<213> ORGANISM: adeno-associated virus 2

<400> SEQUENCE: 3
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccgggt tttacgagat tgtgattaag gtccccagcg    360

```
accttgacga gcatctgccc ggcatttctg acagctttgt gaactgggtg gccgagaagg    420
aatgggagtt gccgccagat tctgacatgg atctgaatct gattgagcag caccccctga    480
ccgtggccga aagctgcag cgcgactttc tgacggaatg gcgccgtgtg agtaaggccc     540
cggaggccct tttctttgtg caatttgaga agggagagag ctacttccac atgcacgtgc    600
tcgtggaaac caccggggtg aaatccatgg ttttggacg tttcctgagt cagattcgcg     660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa atttggaac taaacgggta cgatccccaa tatgcggctt     1260
ccgtctttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact ttcccttcaa cgactgtgtc gacaagatgg    1440
tgatctggtg ggaggagggg aagatgaccg ccaaggtcgt ggagtcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa     1740
aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactc catctttgaa caataaatga tttaaatcag gtatgctgc cgatggttat     2220
cttccagatt ggctcgagga cactctctct gaaggaataa gacagtggtg aagctcaaa     2280
cctgccccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa     2520
gatacgtctt ttgggggcaa cctcggacga gcagtcttcc aggcgaaaaa gagggttctt    2580
gaacctctgg gcctgttga ggaacctgtt aagacggctc cggaaaaaaa gaggccggta     2640
gagcactctc ctgtggagcc agactcctcc tcgggaaccg gaaaggcggg ccagcagcct    2700
```

```
gcaagaaaaa gattgaattt tggtcagact ggagacgcag actcagtacc tgaccccccag    2760 cctctcggac agccaccagc agcccctct ggtctgggaa ctaatacgat ggctacaggc      2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc acccccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg accctgtta ccgccagcag    3660 cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcagggggcc atctgggcaa agattccaca cacggacgga    4080
cattttcacc cctctcccct catgggtgga ttcggactta aacaccctcc tccacagatt    4140
ctcatcaaga acccccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679
```

<210> SEQ ID NO 4
<211> LENGTH: 621
<212> TYPE: PRT
<213> ORGANISM: adeno-associated virus 2

<400> SEQUENCE: 4

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30
```

```
Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
 50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445
```

```
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465             470                 475                     480
Glu His Glu Phe Tyr Val Lys Lys Gly Gly Ala Lys Lys Arg Pro Ala
            485                 490                 495
Pro Ser Asp Ala Asp Ile Ser Glu Pro Lys Arg Val Arg Glu Ser Val
        500                 505                 510
Ala Gln Pro Ser Thr Ser Asp Ala Glu Ala Ser Ile Asn Tyr Ala Asp
            515                 520                 525
Arg Tyr Gln Asn Lys Cys Ser Arg His Val Gly Met Asn Leu Met Leu
    530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
            580                 585                 590
Ile His His Ile Met Gly Lys Val Pro Asp Ala Cys Thr Ala Cys Asp
    595                 600                 605
Leu Val Asn Val Asp Leu Asp Asp Cys Ile Phe Glu Gln
    610                 615                 620
```